(12) United States Patent
Chia et al.

(10) Patent No.: US 9,526,839 B2
(45) Date of Patent: Dec. 27, 2016

(54) INJECTION DEVICE WITH SEALED LUER FITTING

(75) Inventors: Yu Leng Neville Chia, Singapore (SG); Roderick Hausser, Kinnelon, NJ (US); Xua Huyen Nguyen Huu, Singapore (SG); Hoong Sim Lee, Singapore (SG); Hong Tat Teddy Lim, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 358 days.

(21) Appl. No.: 13/383,625

(22) PCT Filed: Jul. 15, 2009

(86) PCT No.: PCT/US2009/004120
§ 371 (c)(1),
(2), (4) Date: Apr. 12, 2012

(87) PCT Pub. No.: WO2011/008190
PCT Pub. Date: Jan. 20, 2011

(65) Prior Publication Data
US 2012/0191067 A1   Jul. 26, 2012

(51) Int. Cl.
*A61M 5/32* (2006.01)
*A61M 5/00* (2006.01)
(Continued)

(52) U.S. Cl.
CPC ........ *A61M 5/282* (2013.01); *A61M 2005/312* (2013.01); *A61M 2005/3104* (2013.01)

(58) Field of Classification Search
CPC ............. A61M 2005/3104; A61M 2005/3106; A61M 2005/311; A61M 2005/312
(Continued)

(56) References Cited

U.S. PATENT DOCUMENTS 2,371,086 A    3/1945 Watson et al.
2,677,373 A    5/1954 Barradas
(Continued)

FOREIGN PATENT DOCUMENTS

DE    102005052545    5/2007
EP    1 961 437       8/2008
(Continued)

OTHER PUBLICATIONS

International Preliminary Report on Patentability dated Jan. 17, 2012 from PCT/US2009/004120.
International Search Report dated Aug. 12, 2010.

*Primary Examiner* — Rebecca E Eisenberg
(74) *Attorney, Agent, or Firm* — The Webb Law Firm

(57) ABSTRACT

The invention relates to an injection device (110) with a luer fitting. The injection device has a compressible syringe body (137) defining a reservoir (146). A male luer fitting (150) has a channel (152) therethrough for conducting contents of the reservoir, and a luer tip at an end of said male luer fitting opposing said base end. A first connecting structure (182) is arranged on said male luer fitting between said base end and said luer tip. A shield cap (160) is arranged on the male luer fitting. The shield cap has a second connecting structure interacting with said first connecting structure to prevent inadvertent movement of said shield cap relative to said male luer fitting when said shield cap is arranged at said first position. A first seal (170) is provided for sealing said channel at said luer tip. A second seal (180) is arranged between said shield cap and said male luer fitting for sealing the outer surface and the luer tip of said male luer fitting from outside contamination.

9 Claims, 20 Drawing Sheets

(51) Int. Cl.
*A61M 5/28* (2006.01)
*A61M 5/31* (2006.01)

(58) Field of Classification Search
USPC .................... 604/192, 195–197, 164.08, 263
See application file for complete search history.

(56) References Cited

U.S. PATENT DOCUMENTS

| | | | |
|---|---|---|---|
| 5,590,798 A * | 1/1997 | O'Connell | 215/48 |
| 6,520,935 B1 | 2/2003 | Jansen et al. | |
| 6,632,199 B1 * | 10/2003 | Tucker | A61M 5/3134 604/192 |
| 7,367,964 B2 * | 5/2008 | Heinz et al. | 604/263 |
| 8,118,788 B2 | 2/2012 | Frezza | |
| 2004/0116869 A1 | 6/2004 | Heinz et al. | |

FOREIGN PATENT DOCUMENTS

| | | |
|---|---|---|
| EP | 1961437 | 8/2008 |
| GB | 789926 | 1/1958 |
| JP | 2009-523522 | 6/2009 |
| WO | WO89/10765 | 11/1989 |
| WO | WO96/14100 | 5/1996 |
| WO | WO2007083034 | 7/2007 |

* cited by examiner

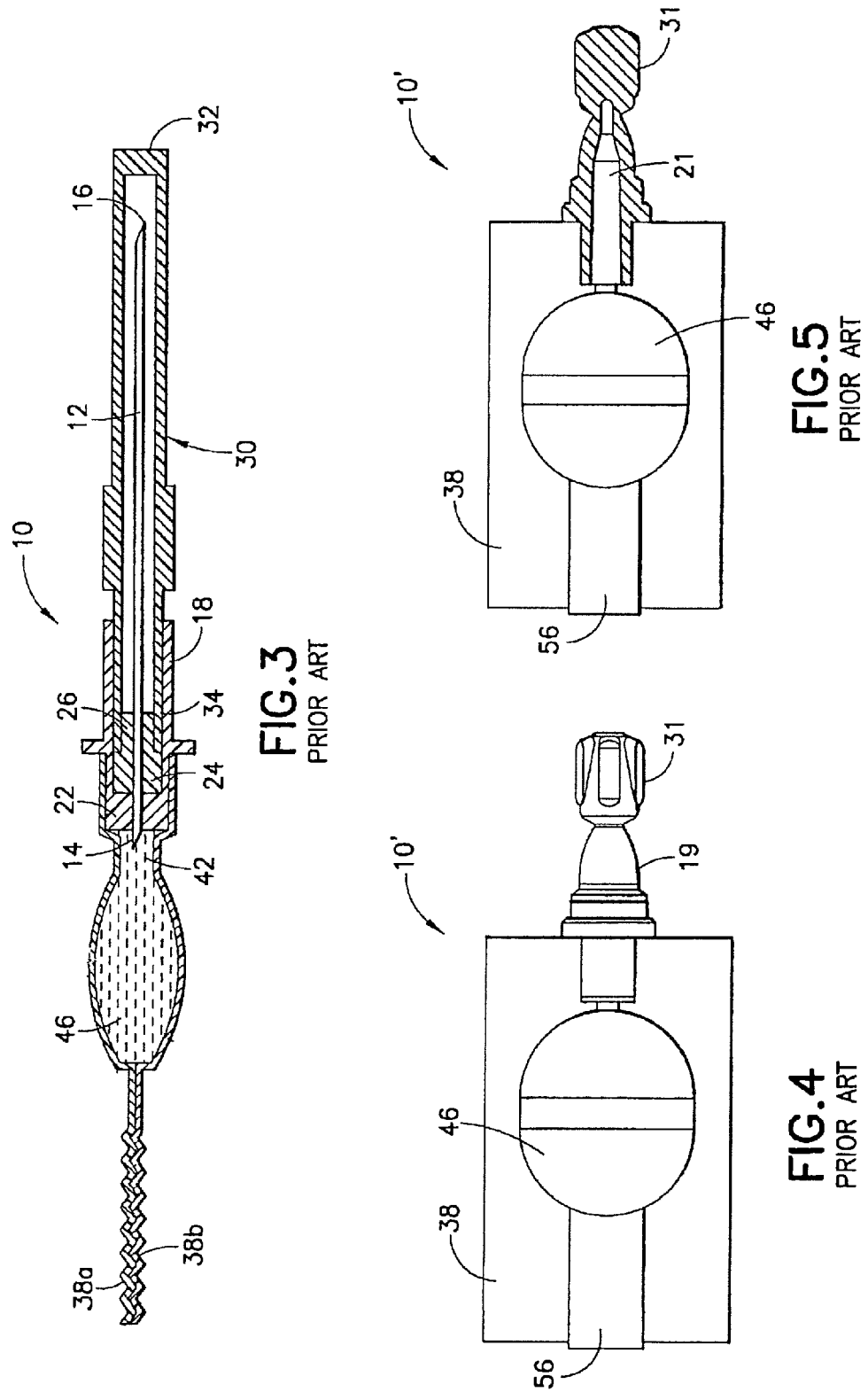

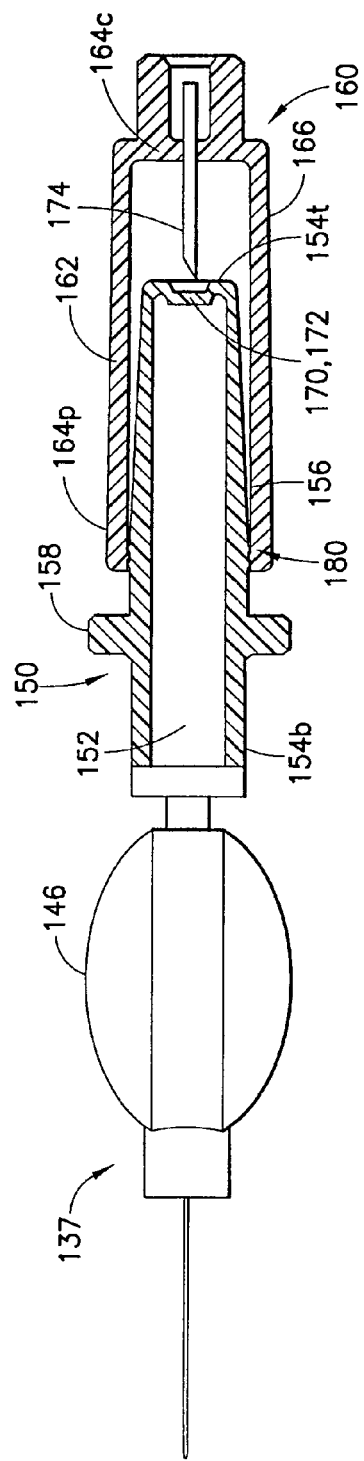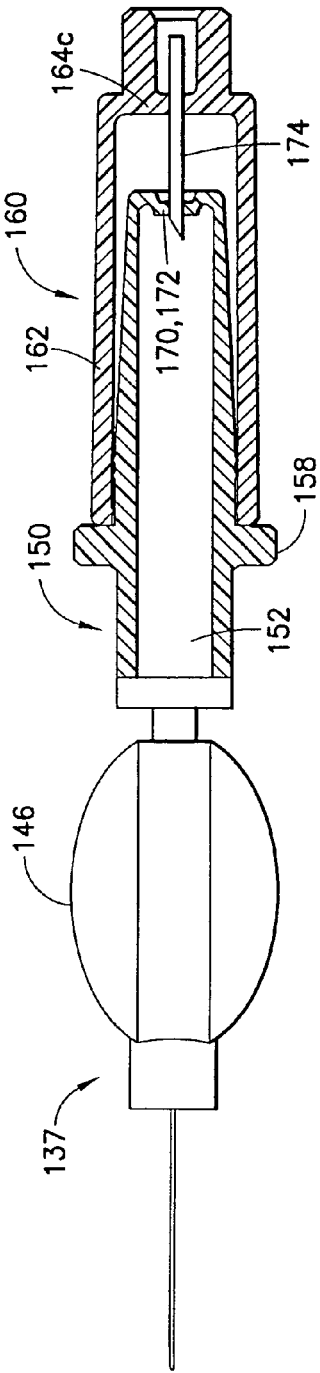
FIG.8
FIG.9

INJECTION DEVICE WITH SEALED LUER FITTING

PRIORITY CLAIM

This is a U.S. national stage of application No. PCT/US2009/004120, filed on Jul. 15, 2009, the content of which is incorporated here by reference.

BACKGROUND OF THE INVENTION

1. Field of the Invention

The present invention relates generally to a prefilled injection device for delivering a dose of medicament by injection and having a sealing system for preventing contamination of the injection device prior to its usage. More particularly, the present invention is directed to a syringe assembly including a sealed luer fitting.

2. Description of the Related Art

Syringes used for the delivery of medicaments to patients are well known. Oftentimes syringes are prefilled with a dosage of a medicament or other substance by a pharmaceutical manufacturer and then distributed to end users such as health care professionals or patients for administration of the prefilled dosage of medicament.

A "compression syringe" used herein refers to a syringe which holds medicament in a reservoir defined by walls with at least one being compressible when squeezed by a user's hand. Compression syringes can be prefilled with a single dose of the medicament, which can be expelled out from the reservoir upon compressing the reservoir. Because of their lightweight and compact properties, their ruggedness and low cost, compression syringes are widely used in many circumstances.

U.S. Pat. No. 4,955,871 discloses a compression syringe 10; the entire content of the U.S. patent is hereby incorporated by reference. As is depicted in FIGS. 1 to 3, a conventional compression syringe 10 has a needle assembly for injecting the medicament into the patient. The needle assembly includes a needle cannula 12 passing through and fastened in a needle hub 20. The needle assembly also includes a nozzle 18 having a closed end connected to an injection port and an open end for holding the needle hub 20. The closed end of the nozzle 18 is formed by a nozzle membrane 22.

The needle cannula 12 of the needle assembly is pointed at both sharp pointed end 14 and tip 16. The sharp pointed end 14 can penetrate nozzle membrane 22 when needle hub 20 is moved toward the nozzle membrane 22. The tip 16 of needle cannula 12 is used to administer the medicament, for example intravenously, or intramuscularly through the skin of a patient.

The needle hub 20 of the needle assembly is made of polystyrene and is preferably secured to needle cannula 12 using an adhesive, such as an epoxy resin. The needle hub 20 can be cylindrical in shape and have a first section 24 of large diameter and a second section 26 of small diameter. The dimensions of large diameter first section 24 and of the internal diameter of a cylindrical nozzle 18 are selected so that needle hub 20 is frictionally held within the cylindrical nozzle 18, but can be moved laterally within the nozzle 18 when a force is applied to needle hub 20, as explained below.

The nozzle 18 of the needle assembly can be cylindrical in shape. An internal rib 28 is formed between nozzle membrane 22 and needle hub 20 to prevent sharp pointed end 14 of the needle cannula 12 from piercing the closed end of the tube unless a sufficient force is applied. The dimensions of internal rib 28 and of large diameter first section 24 are selected so that needle hub 20 will not move past rib 28 unless a sufficient force is applied to needle hub 20. This structure reduces the risk of unintentional piercing of nozzle membrane 22.

The compression syringe 10 has a protector cap 30, which cooperates with the nozzle 18 to enclose and protect the needle cannula 12. The open end 34 of the protector cap 30 is configured to fit inside the nozzle 18 and preferably has an external diameter so selected to be snugly held in position within the nozzle 18. The protector cap 30 is long enough to prevent its closed end 32 from contacting the tip 16 of the needle cannula 12 when the needle cannula 12 is enclosed in the protector cap 30 and the nozzle 18. As a result, the protector cap 30 and the nozzle 18 keep the needle cannula 12 sterile during storage and shipment of the compression syringe 10.

The protector cap 30 and the needle hub 20 cooperate with each other to axially move the needle cannula 12 within the nozzle 18. The internal diameter of open end 34 of the protector cap 30 is selected so that the small diameter second section 26 of needle hub 20 fits snugly within the open end 34 of the protector cap 30. The external diameter of open end 34 of the protector cap 30 is selected so that the protector cap 30 can be moved laterally within the nozzle 18. The protector cap 30 so formed can be used as a tool in which the open end 34 of the protector cap 30 is pushed against the large diameter first section 24 of the needle hub 20. In this way, a sufficient force can be safely applied to the needle hub 20 to force it past internal rib 28. The protector cap 30 then continues pushing large diameter first section 24 of needle hub 20 until sharp pointed end 14 of needle cannula 12 pierces the nozzle membrane 22.

The compression syringe 10 also includes a reservoir 46 for storing medicament and for expelling the medicament into the needle assembly. The reservoir 46 is formed from a pair of flexible sheets 38a and 38b of thermoplastic material. Each sheet 38a, 38b has a central portion 40, an expanded injection neck portion 42, and a substantially flat peripheral portion 44. The peripheral portions 44 of the two sheets 38a, 38b are opposite and coextensive to each other and are sealed together face-to-face to form a reservoir 46. The reservoir 46 can be filled with medicament via a filling neck portion 56 (see FIG. 1) having a filling port 58 as explained more fully in U.S. Pat. No. 4,955,871. Following the filling step, the filling neck portion 56 of the two flexible sheets 38a, 38b are heated sealed together by a sealing portion or region 57 (see FIG. 2).

To activate the compression syringe 10 of FIGS. 1 to 3, the protector cap 30 is pushed back towards the needle hub 20 to cause sharp pointed end 14 of the needle cannula 12 to pierce the nozzle membrane 22, thus placing the needle cannula 12 in fluid communication with the reservoir 46. The protector cap 30 is then removed to expose the tip 16 of the needle cannula 12 for administering an injection to a patient. To administer the medicament, the central portion 40, i.e., the flexible wall of the reservoir 46, is compressed, such as between the thumb and forefinger of the user. After the medicament is administered, the needle cannula 12 is withdrawn from the patient and covered to avoid exposure and possible contamination from the used needle tip 16.

The above described compression syringe 10 is however incompatible with a luer connector and unable to administer the medicament through a luer connector.

FIGS. 4 and 5 show another conventional luer-type syringe 10', which employs a luer fitting 19 to deliver medicament directly to a luer connector. Luer-type syringes 10' are typically sealed by a cap 31, which can be twisted-off to expose the luer channel 21 at the luer tip. Such cap 31 however can be accidentally damaged or removed during shipping or handling of the luer-type syringes 10' causing such syringes 10' unfit for their normal use. In addition, as the luer fitting 19 is intended to be directly fit in a sterile luer connector the luer fitting 19 or the entire syringe 10' must be sealed to protect the luer fitting 19 from contamination prior to the use of the syringe 10'.

These and other disadvantages can adversely affect the operation of such luer-type syringes 10.

Accordingly, there is need for an injection device with a luer fitting so as to be directly insertable into a compatible female luer connector for administering medicament therethrough. In particular, there is need for an injection device with a protected luer fitting that is shielded from contamination during the handling of the injection device.

The embodiments below describe an injection device that is sealed against leakage through its luer tip of content from the medicament reservoir. Additionally or alternatively, the male luer fitting of the injection device is sealed from outside contamination prior to the use of the injection device.

SUMMARY OF THE INVENTION

The present invention relates generally to an injection device for delivering a dose of medicament by injection and having a shield system for preventing contamination of the injection device during its operation. For example, the injection device can be a prefilled compression syringe. The injection device has a syringe body defining a compressible reservoir for containing a dose of medicament. A male luer fitting is provided and has a channel therethrough for conducting contents of the reservoir and is defined by an outer surface, a base end connected to the syringe body, and a luer tip at an end of the male luer fitting opposing the base end. A shield cap is arranged on and sealed against the male luer fitting at a first position prior to use of the injection device. The shield cap can be rotated about or moved along an axis of the male luer fitting during movement from the first position to a second position.

A first seal is provided for sealing the channel at the luer tip of the male luer fitting and preventing leakage therethrough of content from the reservoir at least when the shield cap is at the first position. In one example, the luer tip can be sealed by the first seal in the form of a membrane closing the channel of the male luer fitting. In such a case, the shield cap can be formed with a sharp tip facing the luer tip when the shield cap is in the first position. For example, the sharp tip can comprise a needle bonded to the shield cap. The sharp tip is capable of puncturing or cutting the first seal when the shield cap is moved from the first position to the second position.

In another example, the first seal can be in the form of a twist-off tab, which is joined to the luer tip of the male luer fitting by a weakened or frangible joint. The twist-off tab closes the channel in the male luer fitting in the first position. In one example, one end of the twist-off tab is received in a recess formed in the shield cap when the shield cap is in the first position. The recess defines a shoulder which comes into contact with the twist-off tab during movement of the shield cap from the first position to the second position. The shoulder forces the twist-off tab to twist and subsequently break from the make luer fitting, when the shield cap is moved from the intermediate position to the second position. Upon turning the shield cap from the first position to the second position, the weakened or frangible joint connecting the twist-off tab to the luer tip of the male luer fitting breaks and thus releases the first seal.

The recess in the shield cap can further define a cap flat surface arranged to retain the twist-off tab by friction fit after the twist-off tab is broken from the male luer fitting. In the alternative, the cap flat surface is arranged to retain the twist-off tab when the shield cap is moved from the first position to an intermediate position between the first and second positions.

Optionally, the injection device comprises an alignment indicator indicating alignment of the shield cap with the first position relative to the male luer fitting.

Alternatively, the first seal can be formed by a sealing piece connected in the shield cap and plugged or seated into the channel of the male luer fitting at its luer tip when the shield cap is in the first position. The sealing piece is removed from the channel, when the shield cap is released from the male luer fitting.

A second seal is arranged between the shield cap and the male luer fitting for protecting the outer surface and the luer tip of the male luer fitting from outside contamination when the shield cap is arranged at the first position. The second seal is formed by a first connecting structure formed on the male luer fitting between the base end and the luer tip and a second connecting structure formed on the shield cap. The first and second connecting structures interact with each other to prevent inadvertent movement of the shield cap relative to the male luer fitting when the shield cap is arranged at the first position.

The first and second connecting structures comprise ribs and the second seal is formed by a tortuous path formed by the ribs when the shield cap encloses the male luer fitting in the first position. In one example, the first and second connecting structures comprise circumferential ribs or raised rings. In another example, the first and second connecting structures comprise screw threads, which interlock to form the second seal.

The injection device further comprises a collar connected to the shield cap by frangible tabs when the shield cap is in the first position.

The injection device can further comprise a locking piece arranged proximate the base end of the male luer fitting. The locking piece is configured to interact with collar connected to the shield cap by frangible tabs when the shield cap is in the first position. The locking piece retains the collar during movement of the shield cap from the first position to the second position and causes the frangible tabs to break such that the collar is separated from the shield cap after the shield cap is moved from the first position to the second position. In one example, the locking piece and the collar comprise complementary serrated edges.

The shield cap of the injection device is movable relative to the male luer fitting to the second position from the first position to break one or both of the first and second seals so that the male luer fitting is capable of delivering the contents of the reservoir after the shield cap is removed from the male luer fitting from the second position. In one example, the shield cap is unthreaded during movement from the first position to the second position, thereby lifting the first seal from the luer tip.

The injection device of the invention is hence sealed against leakage through the luer tip of content from the reservoir when the shield cap is in the first position. Additionally or alternatively, the male luer fitting of the injection device is sealed from outside contamination prior to the use of the injection device.

The present invention also relates to a method of dispensing contents of a compressible reservoir of an injection device through a male luer fitting connected to the injection device. The method includes placing a shield cap at a first position on the male luer fitting; sealing, with a first seal, a luer tip preventing leakage therethrough of content from the reservoir of the syringe at least when the shield cap is at the first position; and sealing an outer surface of the luer tip from outside contamination by a second seal formed by first and second connecting structures on the male luer fitting and the shield cap, respectively, when the shield cap is arranged at the first position. For example, the first seal includes a sealing piece seated in an opening on the luer tip when the shield cap is in the first position. The second seal is formed by ribs or circumferential rings arranged on the shield cap and the male luer fitting. In one example, the step of sealing a luer tip can comprise sealing the luer tip with a twist-off tab connected to the male luer fitting by a frangible connection.

During use of the injection device, the shield cap on the male luer fitting is moved from a first position to a second position to open at least the first seal. The shield cap may then be removed from the male luer fitting so that the contents of the reservoir are capable of being dispensed.

The shield cap can be either pulled away from or twisted-off the male luer fitting. Moving the shield cap to the second position can comprise twisting the shield cap relative to the male luer fitting and moving the shield cap longitudinally relative to the male luer fitting.

In a first example, the shield cap includes a sharp tip facing the first seal when the shield cap is in the first position. The sharp tip can cut through or pierce the first seal during movement of the shield cap from the first position to the second position.

In a second example, the method can comprise holding, by the shield cap, the twist-off tab during the step of moving so that the twist-off tab breaks away from the luer tip during movement of the shield cap from the first position to the second position.

In a third example, the second seal is formed by interlocking helical threads on the shield cap and the male luer fitting. The step of moving the shield cap to the second position can comprise twisting the shield cap relative to the male luer fitting to unthread the interlocking threads.

In a fourth example, the shield cap includes a collar connected to the shield cap by frangible tabs when the shield cap is in the first position. The step of moving the shield cap to the second position can further comprise breaking the frangible tabs, wherein the collar remains on the male luer fitting after the step of removing.

These and additional configurations, features, and advantages in connection with the injection device will become more evident through the following detailed description of the embodiments.

BRIEF DESCRIPTION OF THE DRAWINGS

The following description is set forth in connection with the attached drawing figures, which are not necessarily to scale, emphasis instead generally being placed upon illustrating the principles of the invention. In the drawing figures and the following detailed descriptions, wherein similar elements and components are denoted with reference numerals having the same two lower digits throughout the several views and redundant descriptions are omitted:

FIG. 3 is a longitudinal sectional view of the compression syringe shown in FIG. 2;

FIG. 4 is a plan view of the top of another conventional compression syringe in an assembled state;

FIG. 5 is a partial longitudinal sectional view of the luer fitting and the cap of the compression syringe shown in FIG. 4;

FIG. 8 is a longitudinal sectional view of the injection device shown in FIG. 6 and in a first position;

FIG. 9 is a longitudinal sectional view of the injection device shown in FIG. 6 and in a second position;

DETAILED DESCRIPTION OF THE EMBODIMENTS

Figure 1:
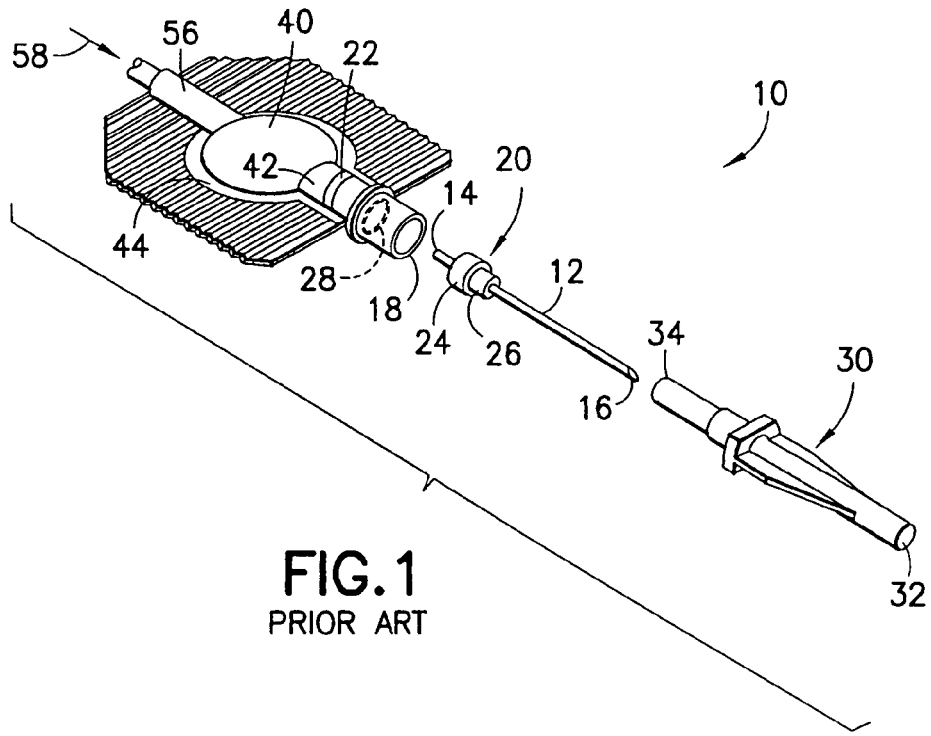
FIG. 1 is an exploded perspective view of a conventional compression syringe.
Figure 2:
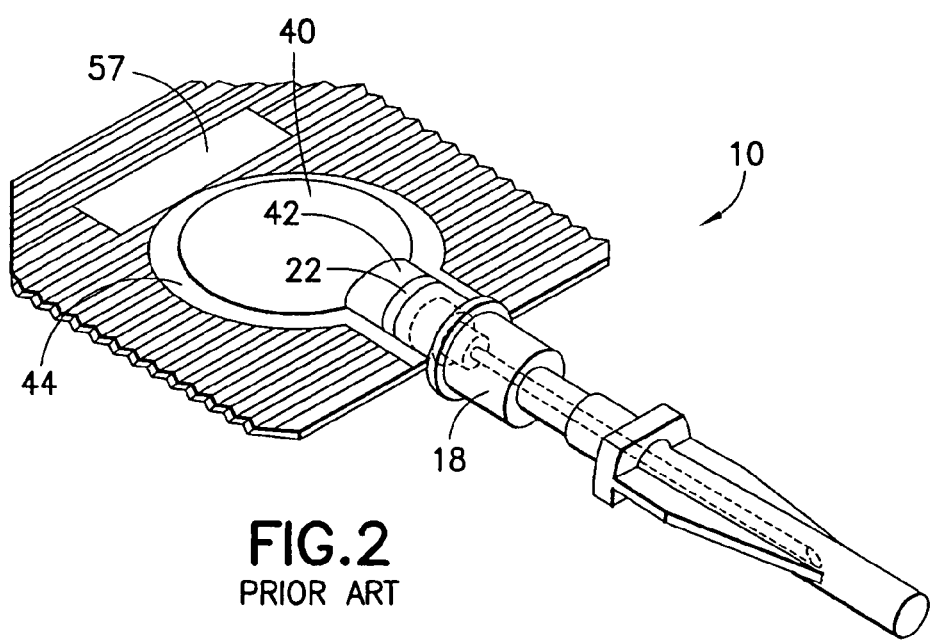
FIG. 2 is a perspective view of the syringe of FIG. 1 in an assembled state.
Figure 6:
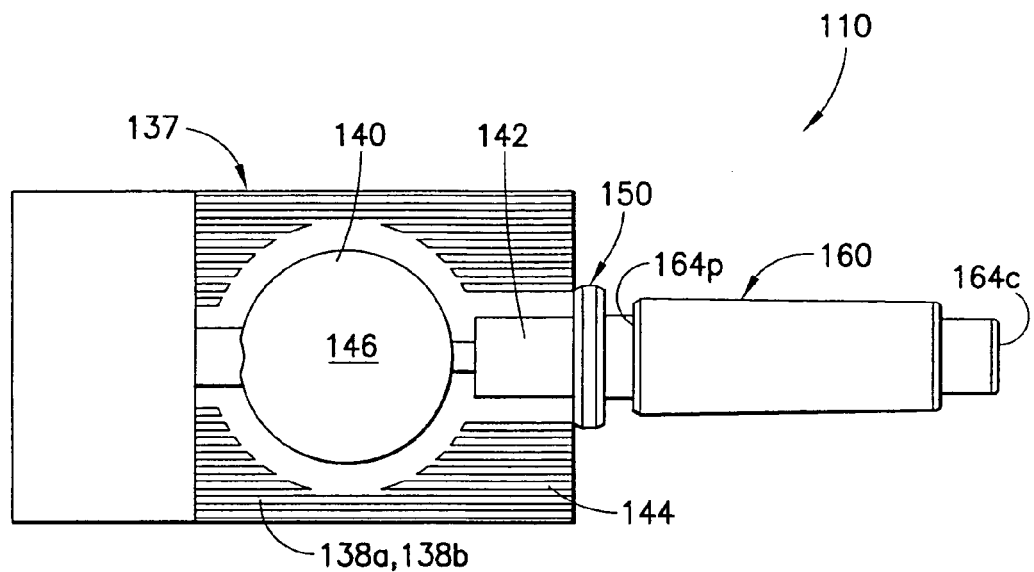
FIG. 6 is a plan view of the top of an assembled injection device shown in an assembled state and formed according to a first embodiment of the invention.
Figure 7:
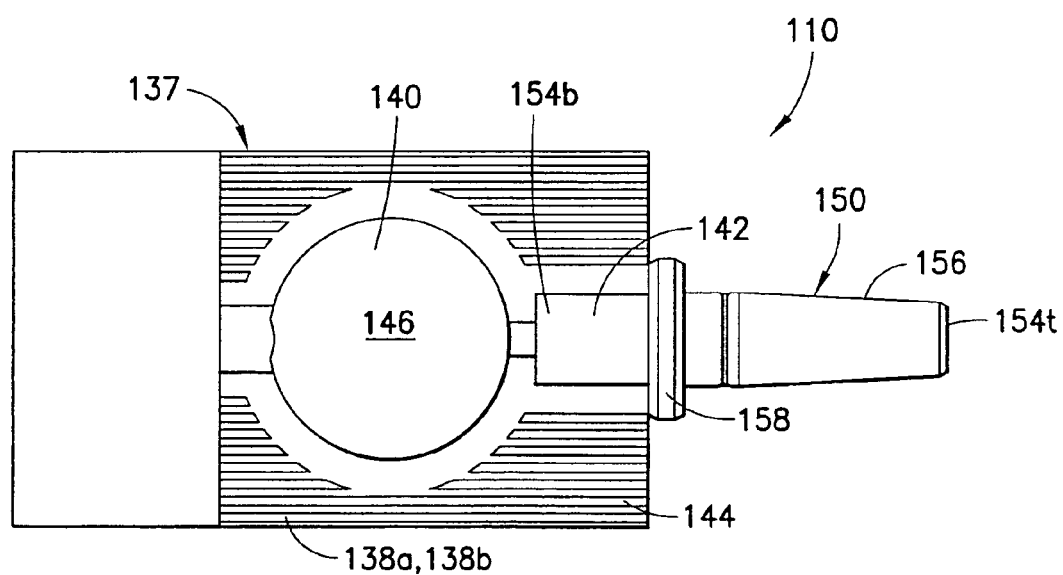
FIG. 7 is a plan view of the top of the injection device shown in FIG. 6 without the shield cap.
Figure 10:
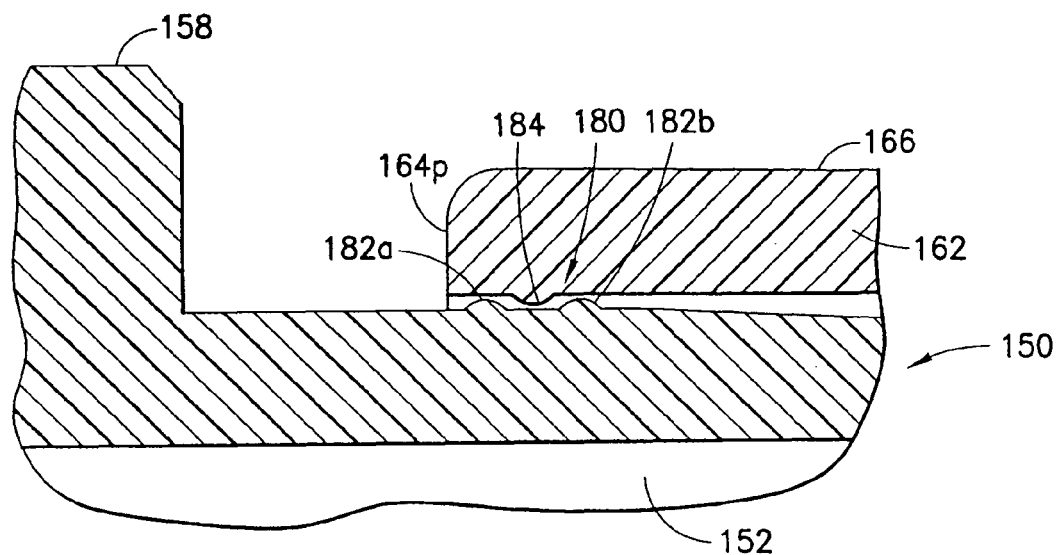
FIG. 10 is a partial longitudinal sectional view of the second seal formed on the injection device of FIG. 6.
Figure 11:
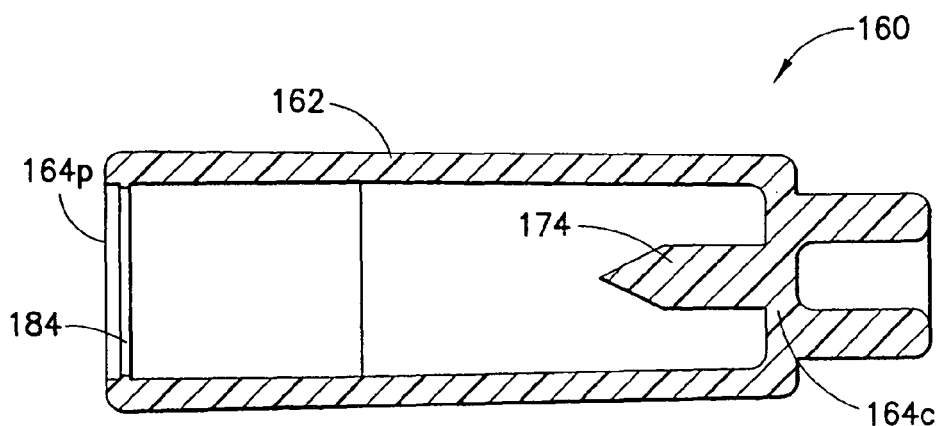
FIG. 11 is a longitudinal sectional view of an alternative shield cap.
Figure 12:
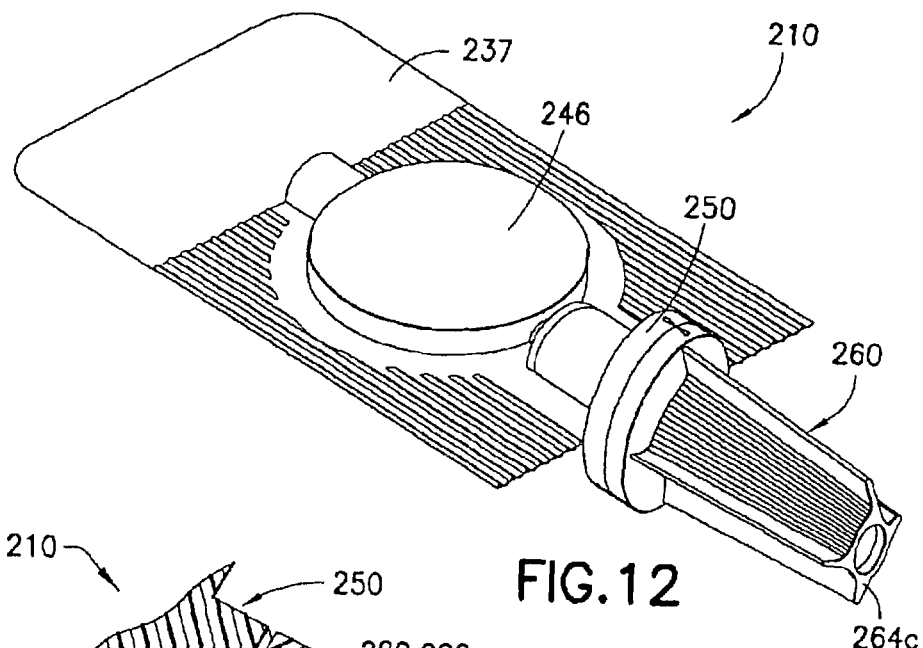
FIG. 12 is a perspective view of an injection device formed in an assembled state and according to a second embodiment of the invention.

The various injection devices described herein are formed to store a dose of medicament and deliver the same by injection. Although compression syringes are shown in the various drawing figures as examples of the injection devices, the invention is not limited to such compression syringes.

FIGS. 6 to 11 illustrate an injection device 110 according to a first embodiment of the invention. The injection device 110 is shown as a compression syringe including a syringe body 137 defining a reservoir 146 for storing medicament. The syringe body 137 is at least partially compressible for expelling the medicament into a male luer fitting 150, which will be described in detail below. The reservoir 146 is formed from a pair of flexible sheets 138a and 138b of thermoplastic material. Each of the sheets 138a, 138b can have a central portion 140, an expanded injection neck portion 142, and a substantially flat peripheral portion 144. At least a portion of the sheets 138a, 138b forming the central portion 140 so that the central portion 140 is compressible. The peripheral portions 144 of the two sheets 138a, 138b are opposite and coextensive to each other and are sealed together face-to-face to form a reservoir 146. The reservoir 146 can be filled with a dosage of medicament via a filling neck portion, during a filling step prior to sealing the two flexible sheets 138a, 138b together as is known.

The male luer fitting 150 of the injection device 110 has an internal channel 152 extending from a base end 154b to a luer tip 154t of the male luer fitting 150. The internal channel 152 is in fluid communication with the reservoir 146 for conducting its contents. The base end 154b of the male luer fitting 150 is sealed to and between the pair of flexible sheets 138a and 138b and in fluid communication with the reservoir 146 via the injection neck portion 142. The male luer fitting 150 can be formed to connect with the reservoir 146 using any known or hereafter developed connection.

The male luer fitting 150 has a contact portion 156 extending from the luer tip 154t toward the base end 154b. The contact portion 156 is formed to be directly fitted inside a female luer connector (not shown) when administering the medicament through such a female luer connector. In an example shown in FIG. 7, the contact portion 156 has a substantially cylindrical shape. The contact portion 156 can be tapered toward the luer tip 154t resulting in a reduced tip for easy handing of the injection device 110 during its assembling and insertion into the luer connector. The taper can be linear or parabolic or have any other curved shape to facilitate the contact portion 156 to be inserted into and connected with a corresponding female luer connector.

The male luer fitting 150 can also have a flange portion 158 between the base end 154b and the contact portion 156. The flange portion 158 has an increased radial dimension relative to the remaining portions of the male luer fitting 150 to facilitate its handling. Optionally, the circumferential surface of the flange portion 158 can be formed with multiple axial ribs or grooves or knurled or otherwise textured to increase traction or grip of the male luer fitting 150 or the entire injection device 110.

The injection device 110 also includes a shield cap 160, which is adapted to fit over at least part of the male luer fitting 150 at a first position prior to use of the injection device 110. The shield cap 160 has a body portion 162 with a closed end 164c and an open end 164p. In the example shown in FIGS. 6 and 8, said shield cap 160 surrounds and encloses the luer tip 154t and the contact portion 156 of the male luer fitting 150 at the first position. In such a first position, the shield cap 160 allows the channel 152 to remain sealed to preserve the contents in the reservoir 146. Additionally or alternatively, the shield cap 160, together with additional sealing means described below, shields the contact portion 156 of the male luer fitting 150 from outside contamination in said first position.

The shield cap 160 can be moved relatively to the male luer fitting 150 from the first position to a second position to release a seal closing the channel 152 at the luer tip 154t of the male bier fitting 150, as will be described in detail below. If desired, the outer surface 166 of the shield cap 160 can be formed with multiple axial ribs or grooves or knurled or otherwise textured to increase traction and facilitate handling of the shield cap 160 or the entire injection device 110.

The injection device 110 can include additional seals to prevent leakage through the luer tip 154 of the male luer fitting 150 of content from the reservoir 146 in the first position. Additionally or alternatively, such additional seals can prevent contamination of the contact portion 156 of the male luer fitting 150 prior to the use of the injection device 110.

As FIGS. 8 and 9 show, a first seal 170 is provided for sealing the channel 152 of the male luer fitting 150 at its luer tip 154 to prevent leakage therethrough of content from said reservoir 146, at least when the shield cap 160 is at said first position. In one example, the first seal 170 can be in the form of a membrane 172 formed at the luer tip 154t to seal the channel 152 inside the male luer fitting 150. Such membrane 172 maintains the channel 152 in a closed or sealed state until the injection device 110 is activated to administer the medicament.

In one embodiment, a piercing element 174, such as a needle or a sharp tip, is used to activate the injection device 110. As FIGS. 8 and 9 show, the piercing element 174 is formed at the closed end 164c of the shield cap 160. The piecing element 174 has a sharp tip oriented toward and aligned with the first seal 170 in an axial direction. When the shield cap 160 is in the first position as is shown in FIG. 8, the piecing element 174 remains in a position without disrupting the first seal 170, such as membrane 172. In one example shown in FIG. 8, the sharp tip of the piercing element 174 faces said luer tip 154t when said shield cap 160 is in said first position. When the shield cap 160 is moved from the first position to the second position as is shown in FIG. 9, the piercing element 174 is urged into the first seal 170 until the first seal 170 is pierced or broken to allow the release of the medicament contained in the reservoir 146.

The piercing element 174 can be formed in various ways. In the examples shown in FIGS. 8 and 9, the piercing element 174 can be separately formed as a needle tip fixed to the closed end 164c of the shield cap 160 by various means, such as bonding and adhesion. In another example shown in FIG. 11, the piercing element 174 can be integrally formed with the shield cap 160, such as through a molding process. Additionally or alternatively, the piercing element 174 can be made of or reinforced with various materials, such as metal or plastics.

The second seal 180 is formed between said male luer fitting 150 and the shield cap 160 when the shield cap 160 is arranged at the first position. The second seal 180 protects the contacting portion 156 and the luer tip 154t of said male luer fitting 150 from outside contamination. In one example best shown in FIG. 10, the second seal 180 includes first and second connecting structures 182, 184 formed on the male luer fitting 150 and the shield cap 160, respectively. For example, the first connecting structure 182, such as circumferential ribs or raised rings 182a, 182b, can be arranged on said male luer fitting 150 between said base end 154b and said luer tip 154t. The second connecting structure 184, such as an internal circumferential rib of raised ring, can be formed inside the shield cap 160. The interlocking of the first and second connecting structures 182, 184 forms a barrier between the male luer fitting 150 and the shield cap 160 and prevents the contact portion 156 of the male luer fitting from being contaminated.

Additionally or alternatively, the second connecting structure 184 interacts with the first connecting structure 182 to prevent inadvertent movement of the shield cap 160 relative to said male luer fitting 150 when said shield cap 160 is arranged at said first position. In one example, the circumferential ridge 184 on the shield cap 160 is fit between the circumferential ribs 182a, 182b on said male luer fitting 150 when the shield cap 160 is in the first position. In such a case, the circumferential rib 182a closer to the base end 154b of the male luer fitting 150 can prevent the shield cap 160 from accidentally moving into the second position and, consequently, damaging the membrane 172 prior to the normal use of the injection device 110. On the other hand, the circumferential ridge 182b closer to the luer tip 154t of the male luer fitting 150 can prevent the shield cap 160 from being accidentally pulled away from the male luer fitting 150 and, consequently, subject its contact portion 156 to contamination.

The injection device 110 can be assembled by placing the shield cap 160 on the contact portion 156 of the male luer fitting 150 in the first position, as is shown in FIG. 8. When doing so, the operator brings the male luer fitting 150 and the shield cap 160 toward each other and pulls the shield cap 160 over the luer tip 154t and then the contact portion 156 of the male luer fitting 150. When the circumferential rib 184 on the shield cap 160 comes in contact with the circumferential rib 182b on the male luer fitting 150, the operator applies a gentle force to urge the circumferential rib 184 to pass the circumferential rib 182b. The circumferential rib 184 on the shield cap 160 thus falls between the two circumferential ribs 182a, 182b on said male luer fitting 150 and bring the shield cap 160 into the first position.

A description of exemplary usage of the injection device 110 of the present invention is provided below. It should be understood by a person of ordinary skill in the art that the following description is provided as an illustrative and non-limiting example.

When activating the injection device 110, an operator moves the shield cap 160 further onto the male luer fitting 150 from the first position toward the second position. The movement urges the circumferential rib 184 on the shield cap 160 to pass the circumferential rib 182a on the male luer fitting until the piercing element 174 is forced into the membrane 172 to pierce or break through the same at the second position. The shield cap 160 can then be removed from the male luer fitting 150 from said second position to expose the contact portion 156 and luer tip 154t. The male luer fitting is then inserted in a female luer connector (not shown). The operator then digitally compresses the reservoir 146, for example, between a thumb and a forefinger, to deliver the contents of the reservoir 146.

The used shield cap 160, together with the piercing element 174 fixed to the closed end 164c of the shield cap 160, can then be either disposed or sterilized for further use. In one example, the used shield cap 160 can be reassembled with the used syringe body 137 and disposed together. In another example, the used shield cap 160 can be reassembled with the used syringe body 137 and stored for a future use of the remaining drug. In a further example, the used shield cap 160 can be sterilized and assembled with another new syringe body 137.

The first and second connecting structure 182, 184 and seals 170, 180 may alternatively be formed in various other manners as described in additional embodiments below.

FIGS. 12 to 16 illustrate an injection device 210 formed according to a second embodiment of the invention. In this embodiment, the syringe body 237, the male luer fitting 250, and the shield cap 260 are similarly formed to their respective counterparts 137, 150, and 160 described in the first embodiment. Only the differences between the first and second embodiments are described in details below.

Figure 13:
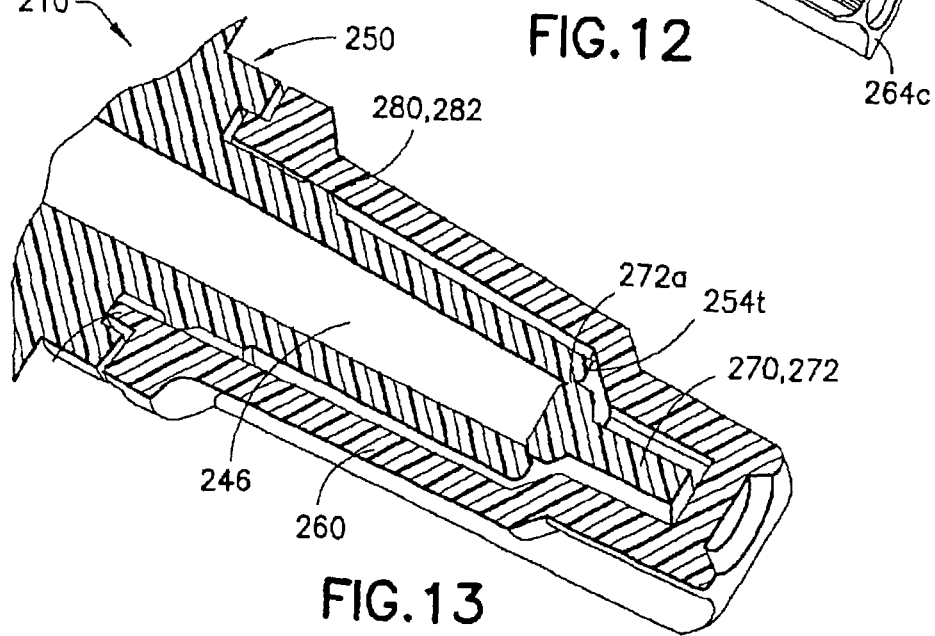
FIG. 13 is a partial longitudinal sectional view of the injection device in FIG. 12.
Figure 13A:
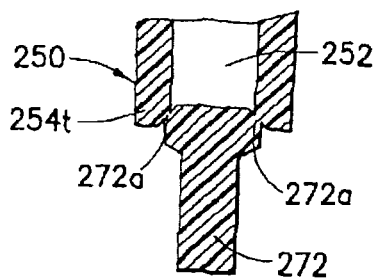
FIGS. 13A and 13B are partial longitudinal sections showing a twist-off tab being joined to and detached from the luer tip of the male luer fitting shown in FIG. 13.
Figure 13B:
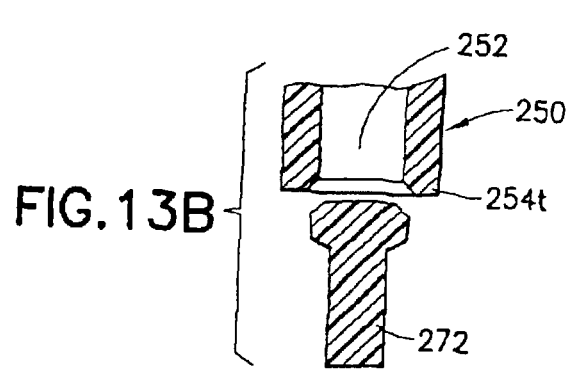
Figure 16:
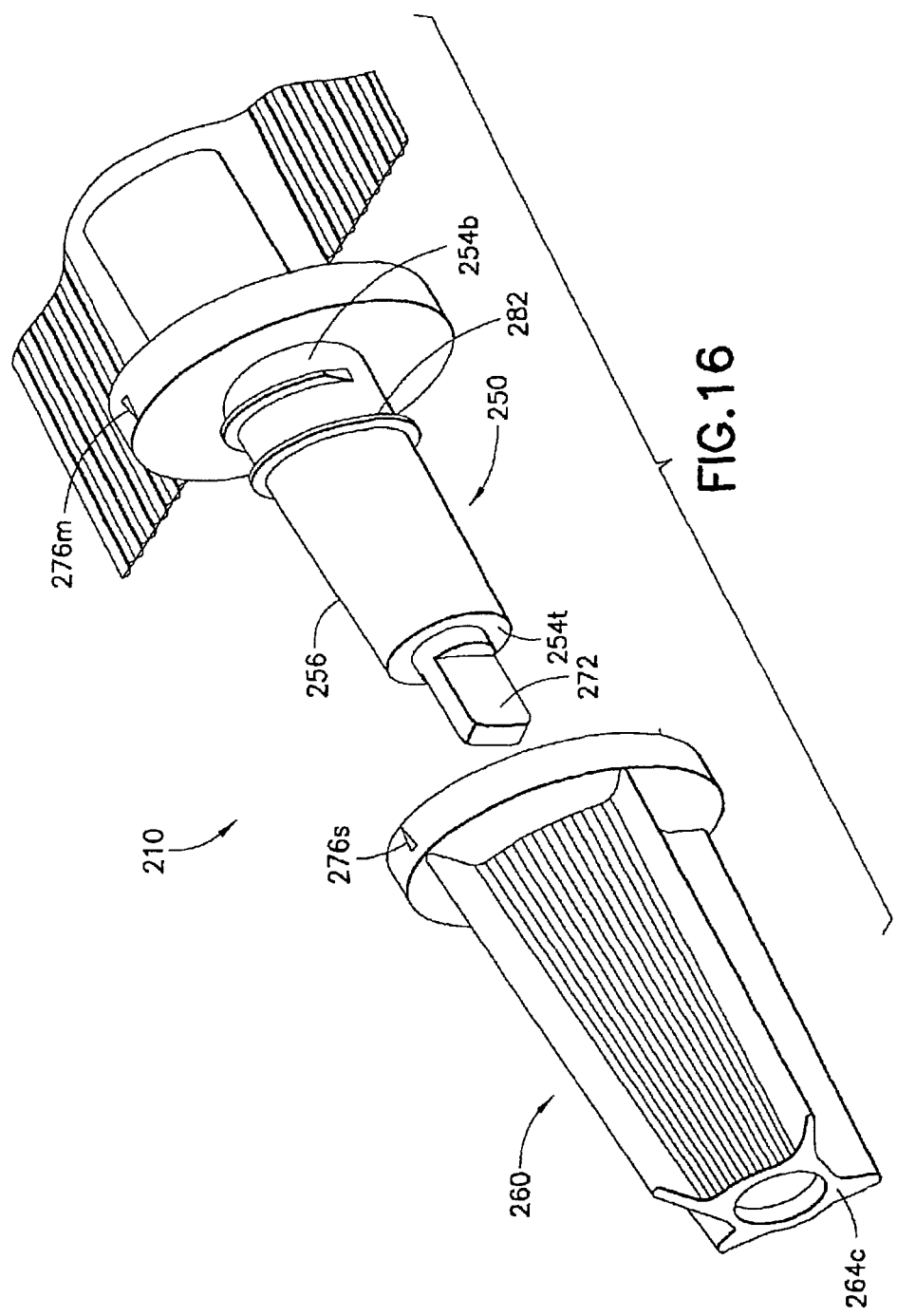
FIG. 16 is a partial exploded perspective view of the injection device in FIG. 12.
Figure 17:
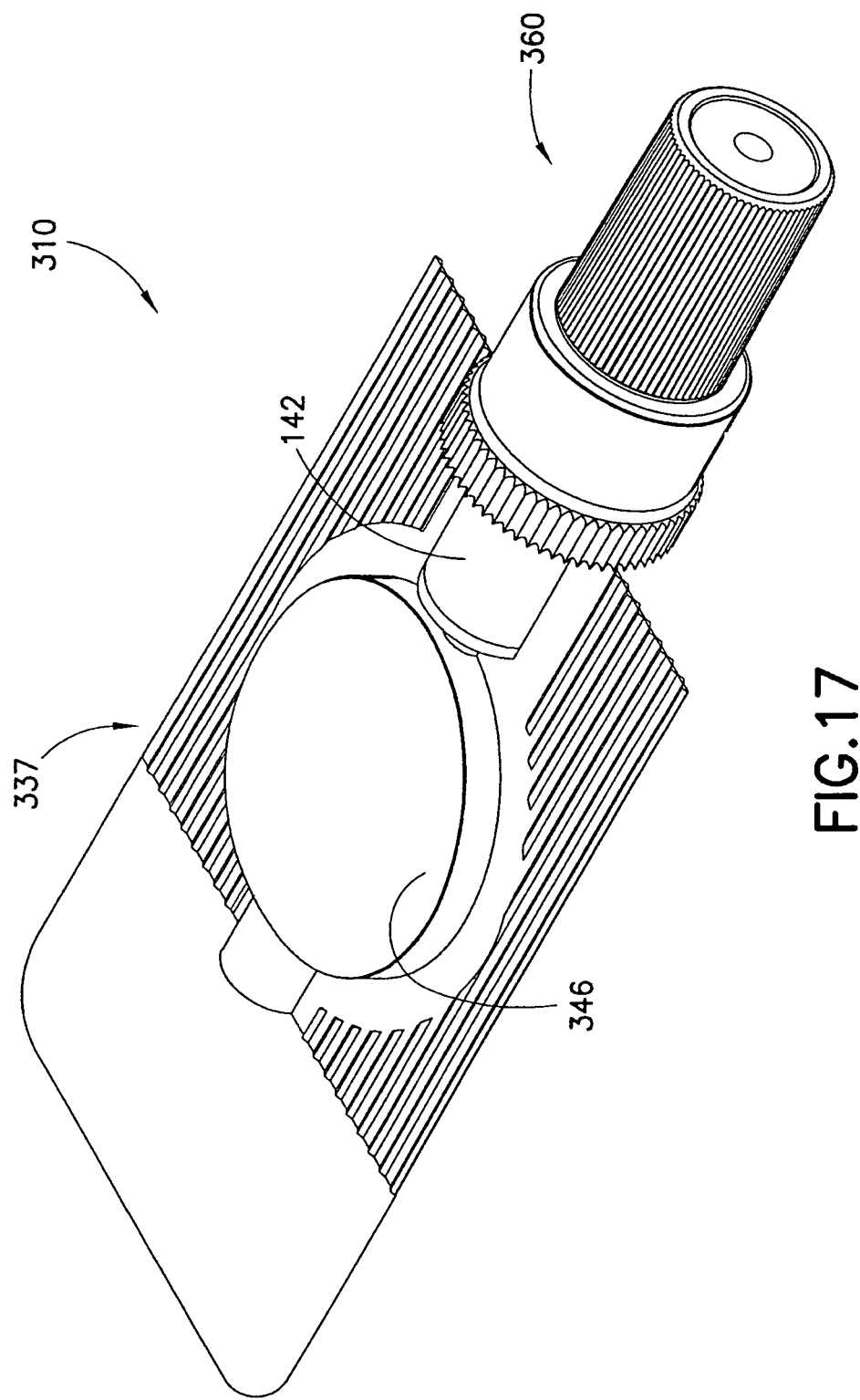
FIG. 17 is a perspective view of an injection device formed in an assembled state and according to a third embodiment of the invention.

As is shown in FIGS. 13 and 16, the first seal 270 in this embodiment is in the form of a twist-off tab 272 connected to the luer tip 254 to seal the channel 252 in the male luer fitting 250. As is best shown in FIG. 13A, the twist-off tab 272 is joined to the luer tip 254 through a weakened or frangible portion 272a. As is described in details below and shown in FIG. 13B, the weakened or frangible portion 272a can be severed or broken off when activating the injection device 210 to administer the medicament contained in the reservoir 246.

Figure 14:
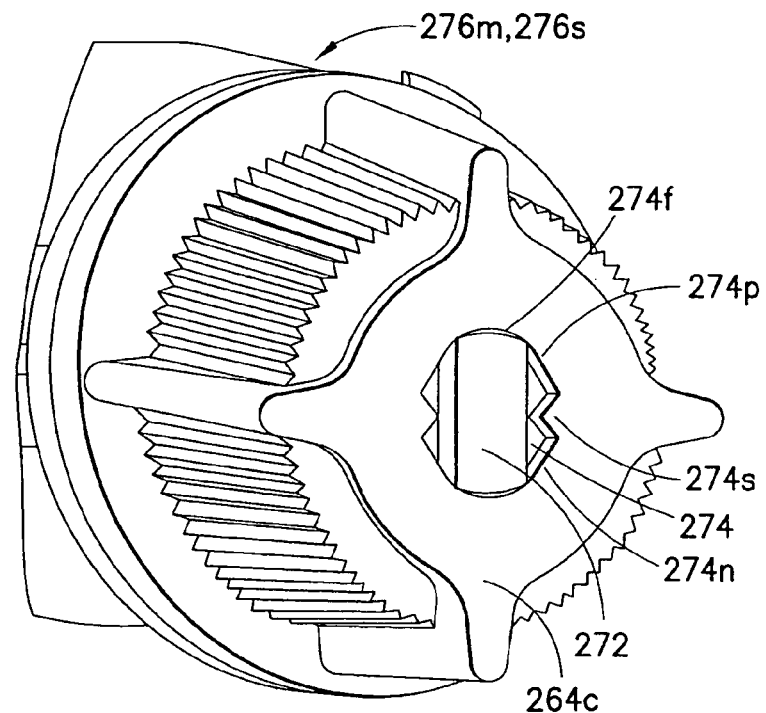
FIG. 14 is a partial perspective view of the injection device shown in FIG. 12 and in a first position.
Figure 15:
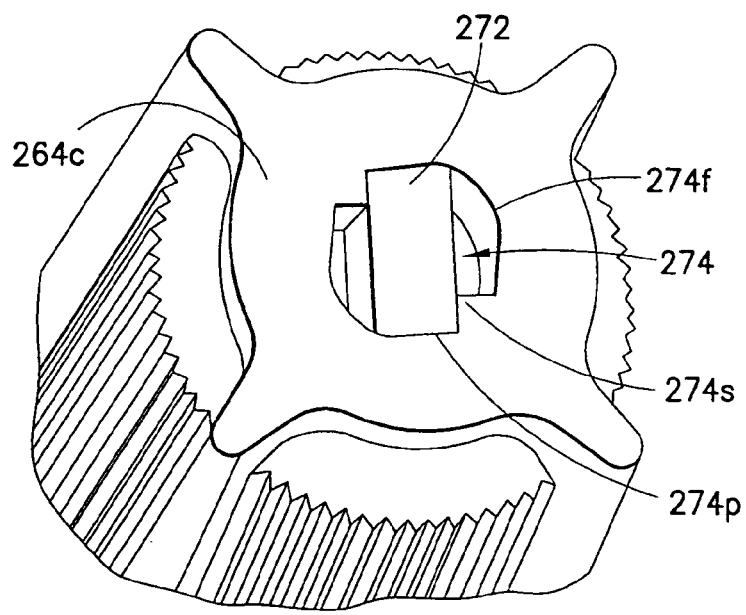
FIG. 15 is a partial perspective view of the injection device shown in FIG. 12 and in a second position.

To facilitate the removal of the twist-off tab 272 when activating the injection device 210, a clamping element 274 is provided and in the form an internal recess in the closed end 264c of the shield cap 260. As is shown in FIGS. 14 and 15, the recess 274 has a contoured circumference including a pair of radially opposite first walls 274f formed to accommodate the twist-off tab 272 therebetween. The radially opposite first walls 274f are spaced apart so that they do not interfere with the twist-off tab 272 after such tab 272 is placed between the first walls 274f in a first position.

The contoured circumference of the recess 274 also includes a pair of radially opposite clamping walls 274p circumferentially adjacent the first wall 274f in a circumferential direction, and an additional pair of radially opposite clamping walls 274n circumferentially adjacent the first wall 274f in an opposite circumferential direction. Each pair of the radially opposite clamping walls 274p, 274n are spaced from each other for a distance less than the larger radial dimension of the twist-off tab 272. When the shield cap 260 is rotated in relation to the male luer fitting 250 to align with the adjacent radially opposite clamping walls 274p, 274n, the twist-off tab 272 on the male luer fitting 250 is radially clamped between one of the pairs of radially opposite clamping walls 274p, 274n.

Additionally, one or more shoulders 274s are formed on the contoured circumference and extend radially towards each other. The shoulders 274s can serve as a severance means for the twist-off tab 272 when the shield cap 260 moves from the first position to a second position. In one example, when the shield cap 260 continues to rotate in relation to the male luer fitting 250, the twist-off tab 272 abuts the shoulders 274s and is forced to rotate in relation to the mail luer fitting 250 by the shoulders 274s until the weakened or frangible portion 272a breaks. The severed twist-off tab 272 remains in the recess 274 held by the radially opposite clamping walls 274p, 274n and can be removed from the male luer fitting 250 together with the shield cap 260.

As is shown in FIG. 16, the second seal 280 can be in the form of one or more ribs, rings, bumps, or other protrusions formed on the male luer fitting 250 between said base end 254b and said luer tip 254t. In one example, the second seal 280 includes one or more tortuous path ribs 282 adapted to frictionally engage the interior wall of the shield cap 260, thereby providing a seal between the male luer fitting 250 and the shield cap 260 and preventing alien matter from entering the shield cap 260 and contaminating the contact portion 256 of the male luer fitting 250. As a result, the shield cap 260 is held in place on the male luer fitting 250 in the first position. As one skilled in the will appreciate, the tortuous path ribs 282 can alternatively or additionally be formed on the interior wall of the shield cap 260 to frictionally engage the male luer fitting 250.

When assembling the injection device 210, the male luer fitting 250 and the shield cap 260 are brought toward and aligned with each other. For example, the twist-off tab 272 on the male luer fitting 250 is to be aligned with the radially opposite first walls 274f in the closed end 264c of the shield cap 260. To facilitate the alignment, the male luer fitting 250 and the shield cap 260 can be provided with alignment marks, such as orientation lines 276m, 276s, respectively. After the shield cap 260 fully fits over the contact portion 256 on the male luer fitting 250 in the first position, the twist-off tab 272 is positioned between the radially opposite first walls 274f in the closed end 264c of the shield cap 260.

A description of exemplary usage of the injection device 210 of the present invention is provided below. It should be understood by a person of ordinary skill in the art that the following description is provided as an illustrative and non-limiting example.

To activate the injection device 210, the shield cap 260 is rotated relatively to the male luer fitting 250 either clockwise or counterclockwise. Such relative rotation drives the twist-off tab 272 in between a pair of the radially opposite clamping walls 274p, 274n in the shield cap 260. As a result, the twist-off tab 272 is squeezed or pinched by the radially opposite clamping walls 274p, 274 and held thereby. The shield cap 260 is then further rotated in relation to the male luer fitting 250 and the shoulders 274s carry the twist-off tab 272 along in the rotation until the weakened or frangible portion 272a breaks. The shield cap 260, together with the twist-off tab 272 held by the radially opposite clamping walls 274p, 274n, is then removed from the male luer fitting 250 to expose the contact portion 256 and luer tip 254t. The male luer fitting 250 is then inserted in a female luer connector (not shown). Once inserted the operator squeezes the reservoir 246 to administer the medicament.

The first and second seals 270, 280 can alternatively be formed by the various connecting structures and seals described in the other embodiments of the present application.

FIGS. 17 to 25 illustrate an injection device 310 formed according to a third embodiment of the invention. In this embodiment, the syringe body 337, the male luer fitting 350, and the shield cap 360 are similarly formed to their respective counterparts 137, 150, and 160 described in the first embodiment. Only the differences between the third embodiment and the previous embodiments are described in details below.

Figure 18:
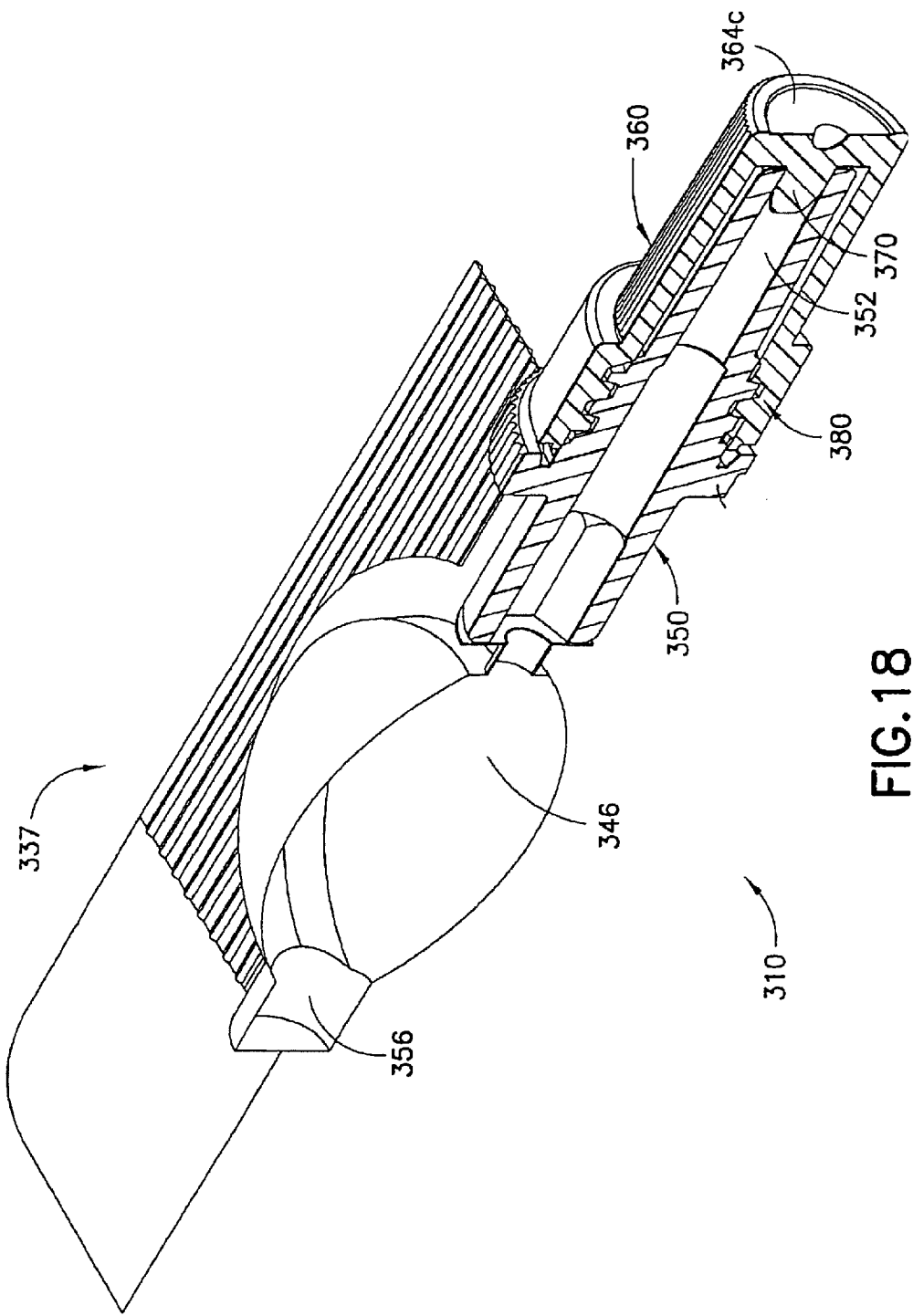
FIG. 18 is a longitudinal sectional view of the injection device shown in FIG. 17.
Figure 19:
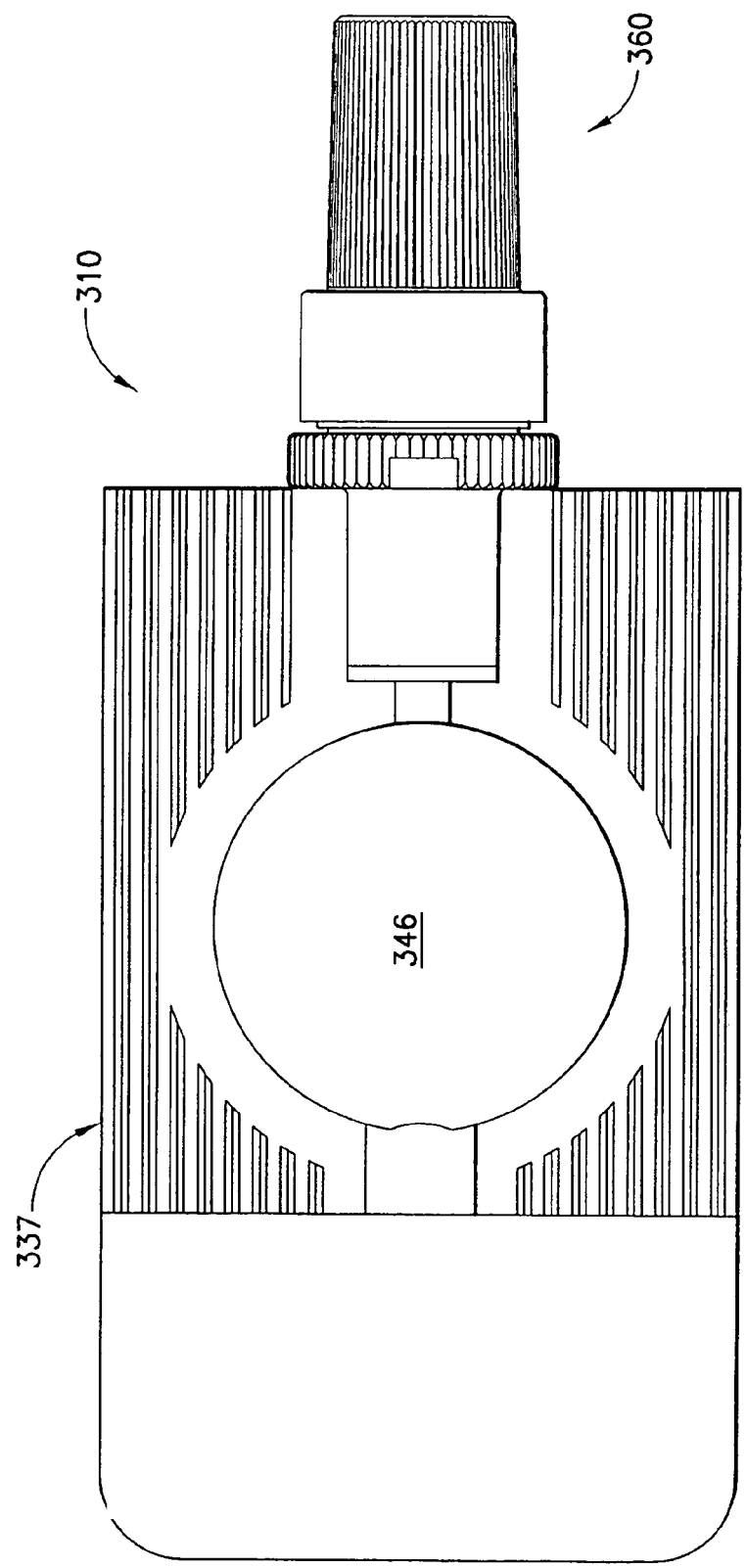
FIG. 19 is a plan view of the top of the injection device shown in FIG. 17.
Figure 20:
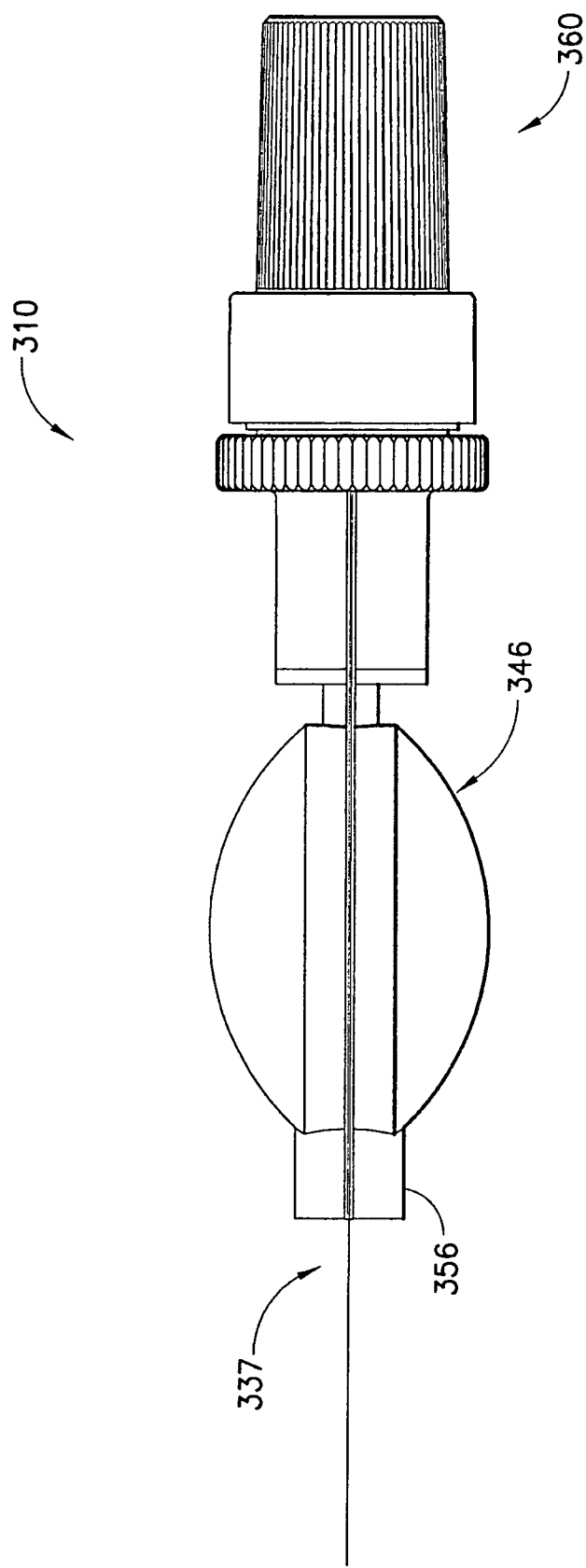
FIG. 20 is a side view of the injection device shown in FIG. 17.
Figure 21:
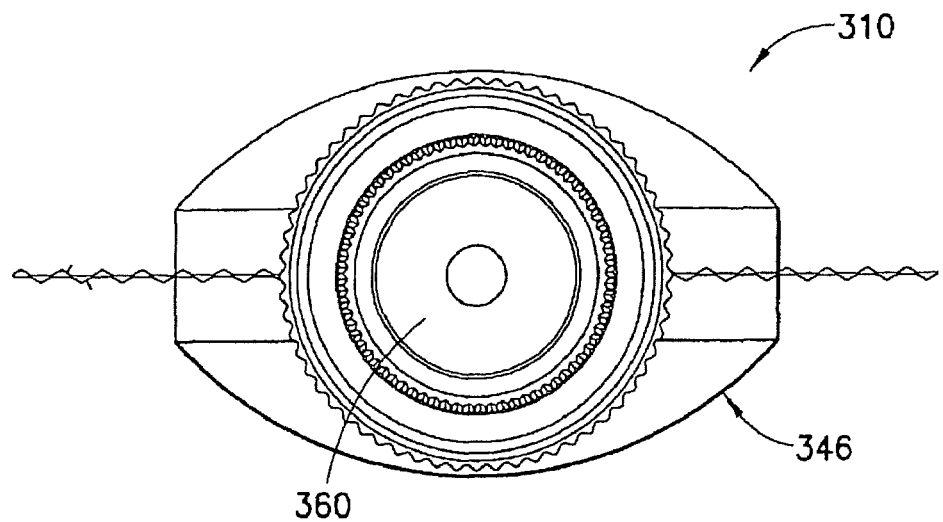
FIG. 21 is a front end view of the injection device shown in FIG. 17.
Figure 22:
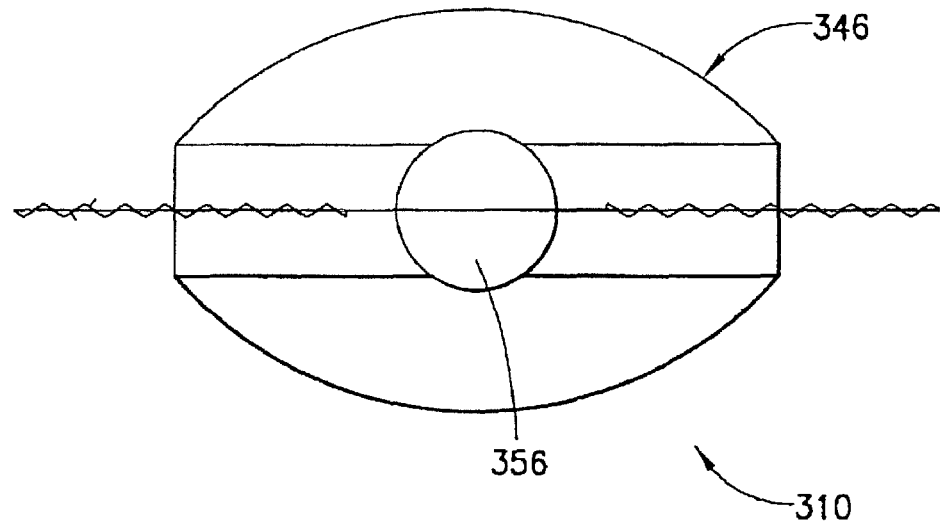
FIG. 22 is a rear end view of the injection device shown in FIG. 17.
Figure 23:
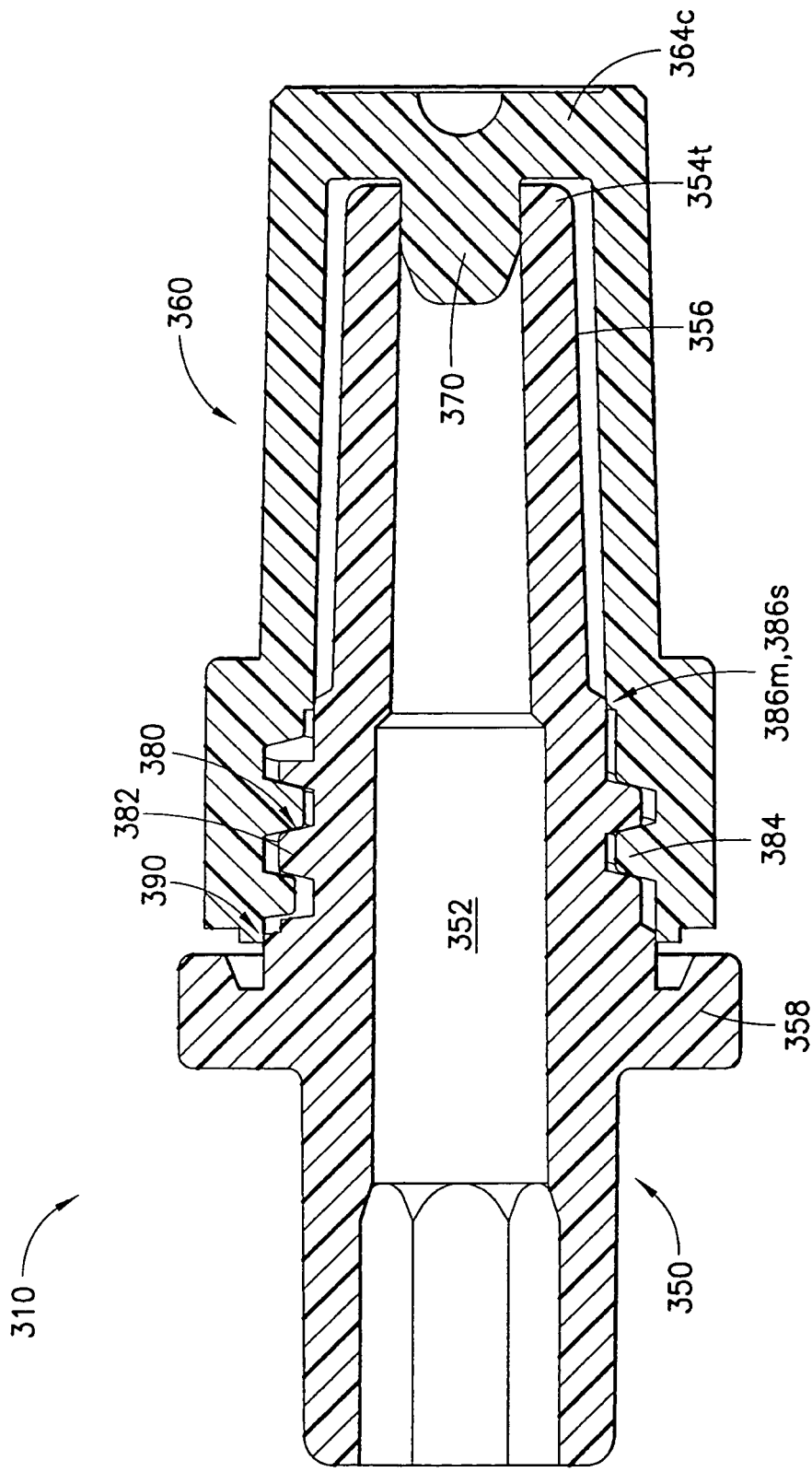
FIG. 23 is a partial longitudinal sectional view of the injection device shown in FIG. 17 and in a first position.

A first seal 370 is formed at a closed end 364c inside the shield cap 360. The first seal 370 is in the form of a protrusion toward and aligned with a channel 352 in the male luer fitting 350 in an axial direction. In the first position, as is shown in FIGS. 18 and 23, the first seal 370 is plugged or seated in the channel 352 at the luer tip 354t of the male luer fitting 350. The first seal 370 prevents leakage of medicament from the syringe body 337. As is described below, when the shield cap 360 is moved from the first position to the second position, the first seal 370 is removed or unseated from inside the channel 352 to allow the release of the medicament contained in the reservoir 346.

The second seal 380 in this embodiment can comprise matching helical threads 382, 384 formed on the respective male luer fitting 350 and shield cap 360. In the example shown in FIG. 23, the shield cap 360 has an enlarged open end 364, inside which the thread 384 is formed. The matching threads 382, 384 are capable of engaging with each other to seal the contact portion 356 of the male luer fitting 350 from outside contamination. Additionally or alternatively, the second seal 380 can prevent the first seal 370 from being accidentally pulled out from the channel 352 and thus at least partially operate as a fastening means for the first seal 370.

Figure 24:
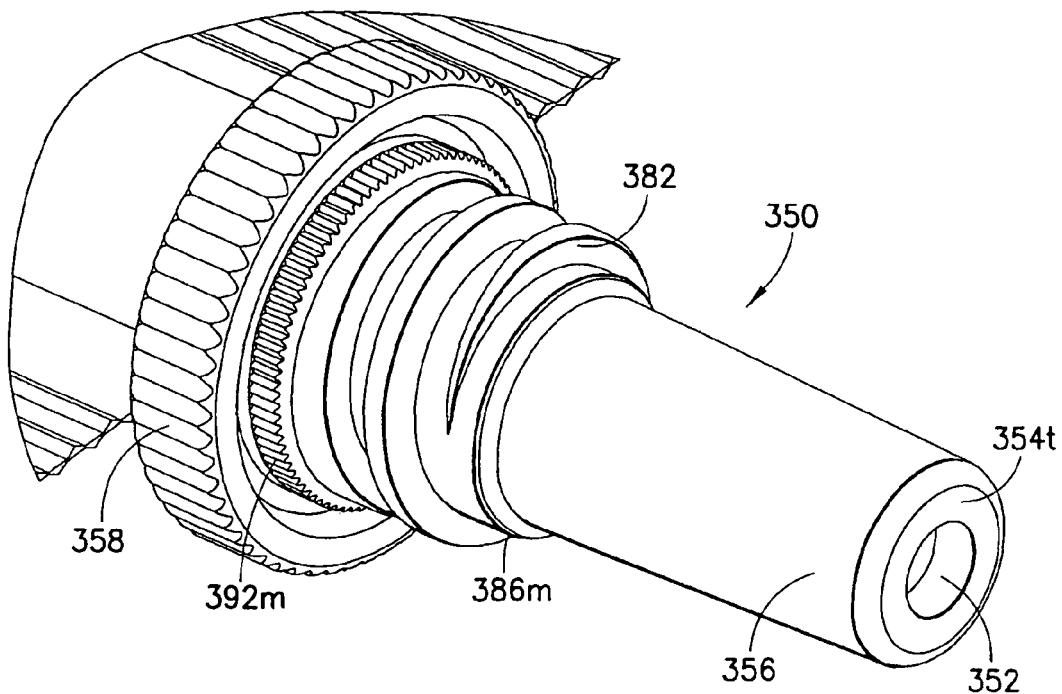
FIG. 24 is a partial perspective view of the male luer fitting of the injection device shown in FIG. 17.
Figure 25:
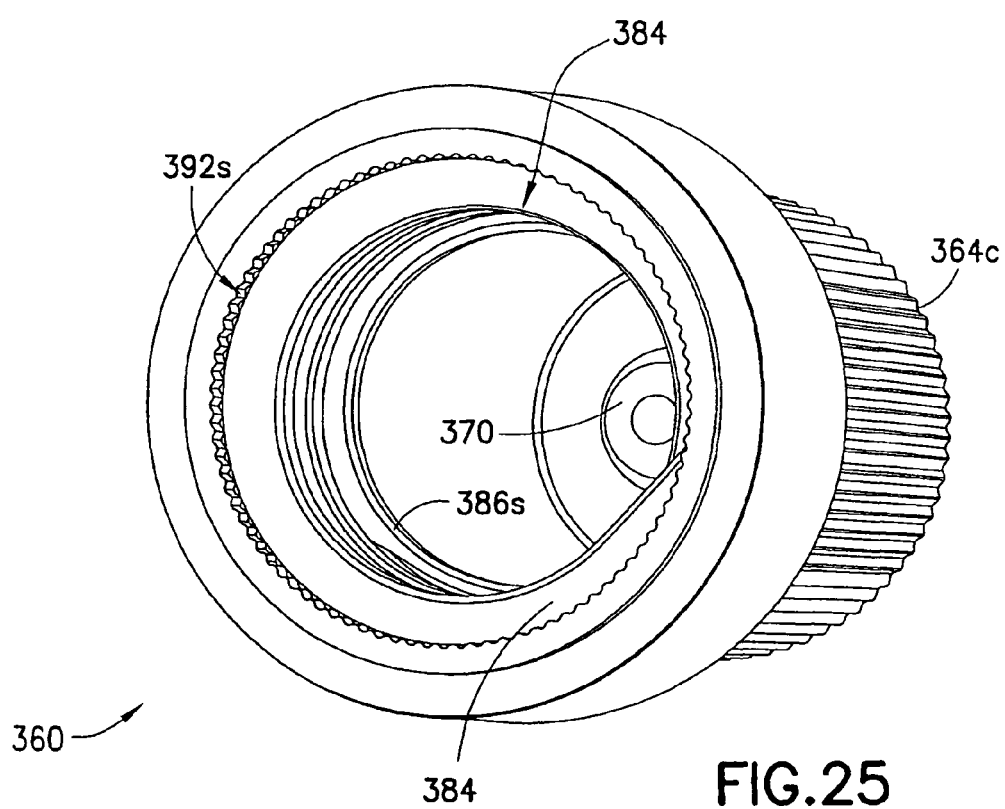
FIG. 25 is a perspective view of the shield cap of the injection device in FIG. 17.
Figure 26:
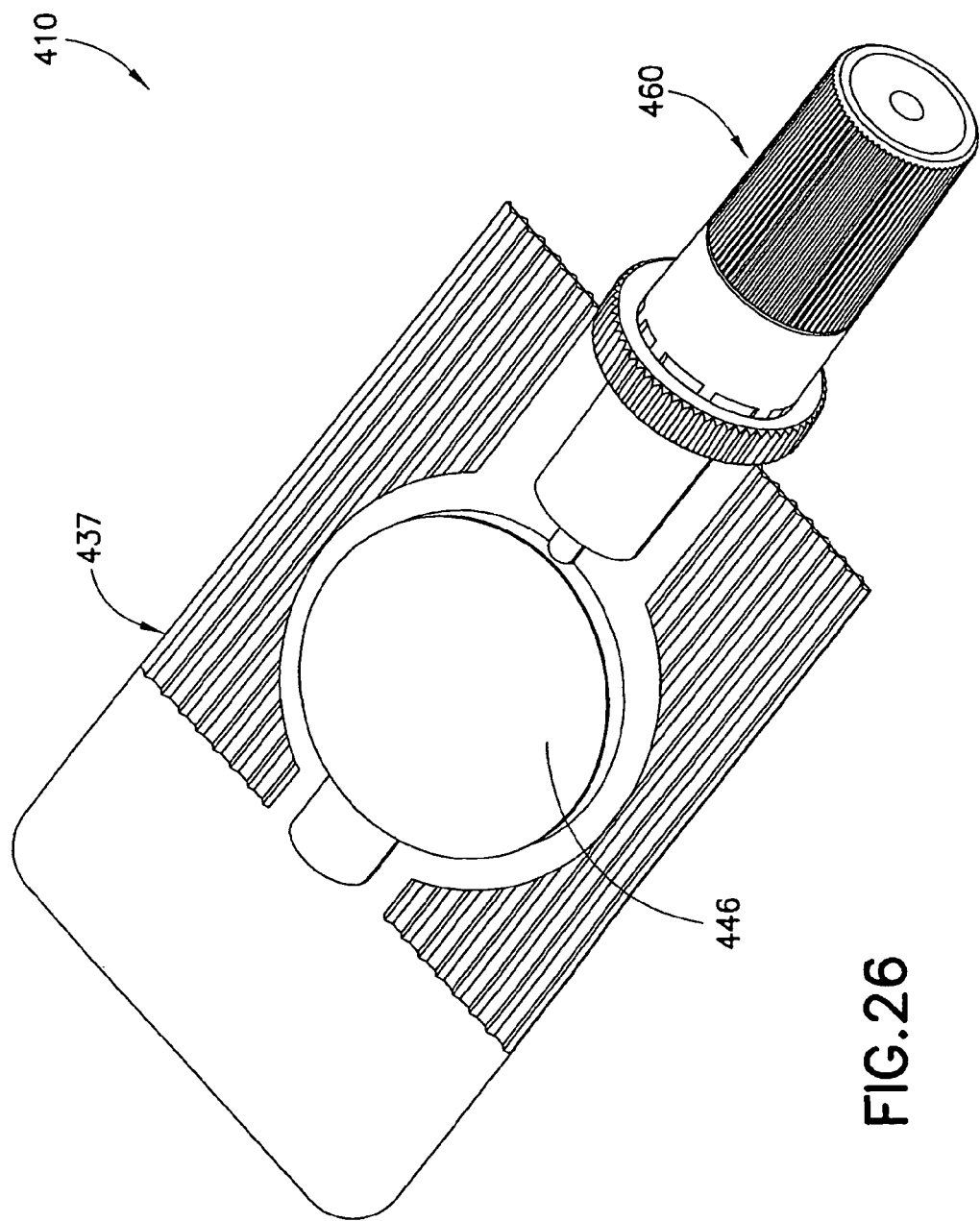
FIG. 26 is a perspective view of a variation of the injection device in the third embodiment in an assembled state.
Figure 27:
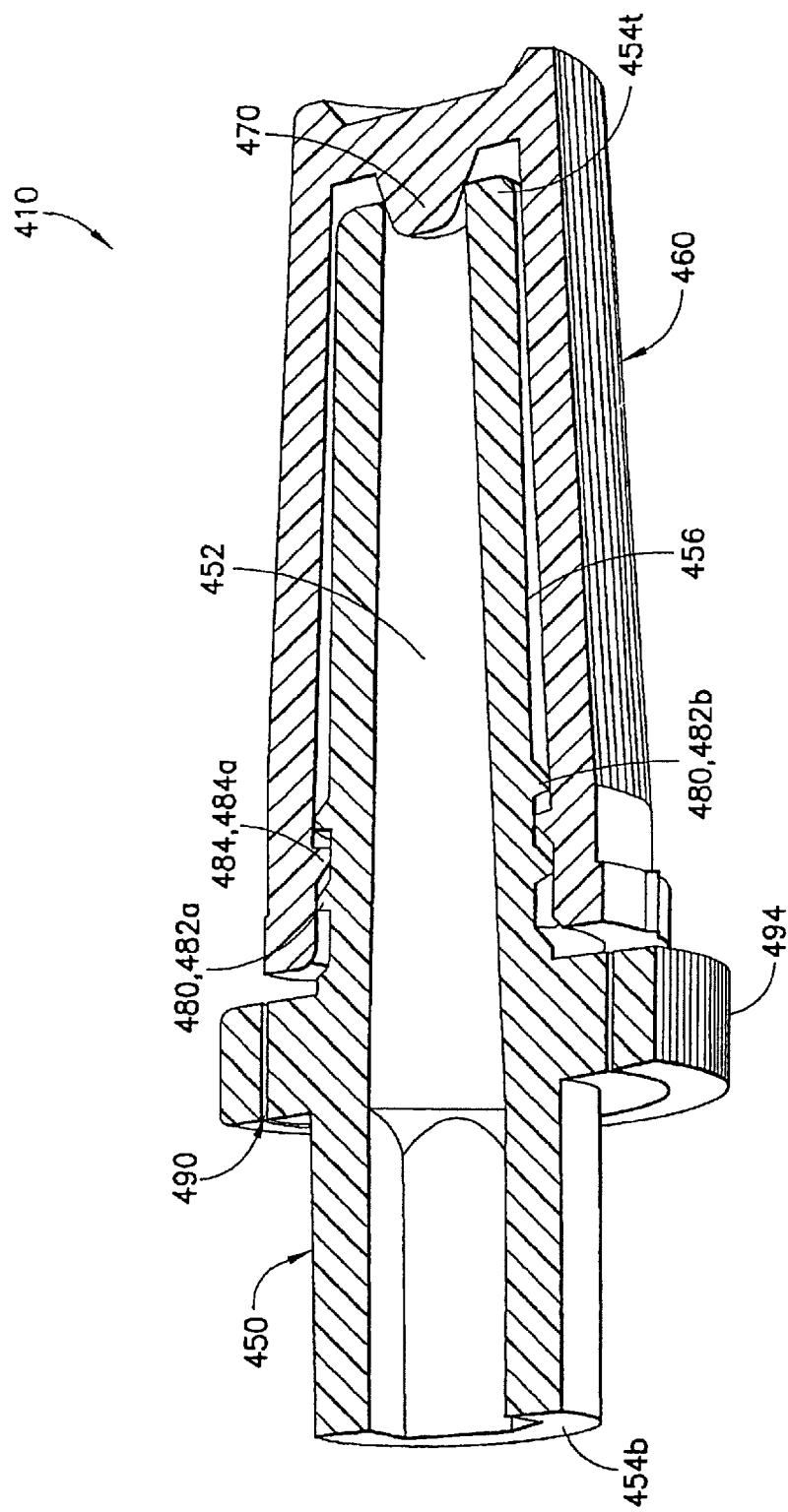
FIG. 27 is a partial longitudinal sectional view of the injection device in FIG. 26.
Figure 28:
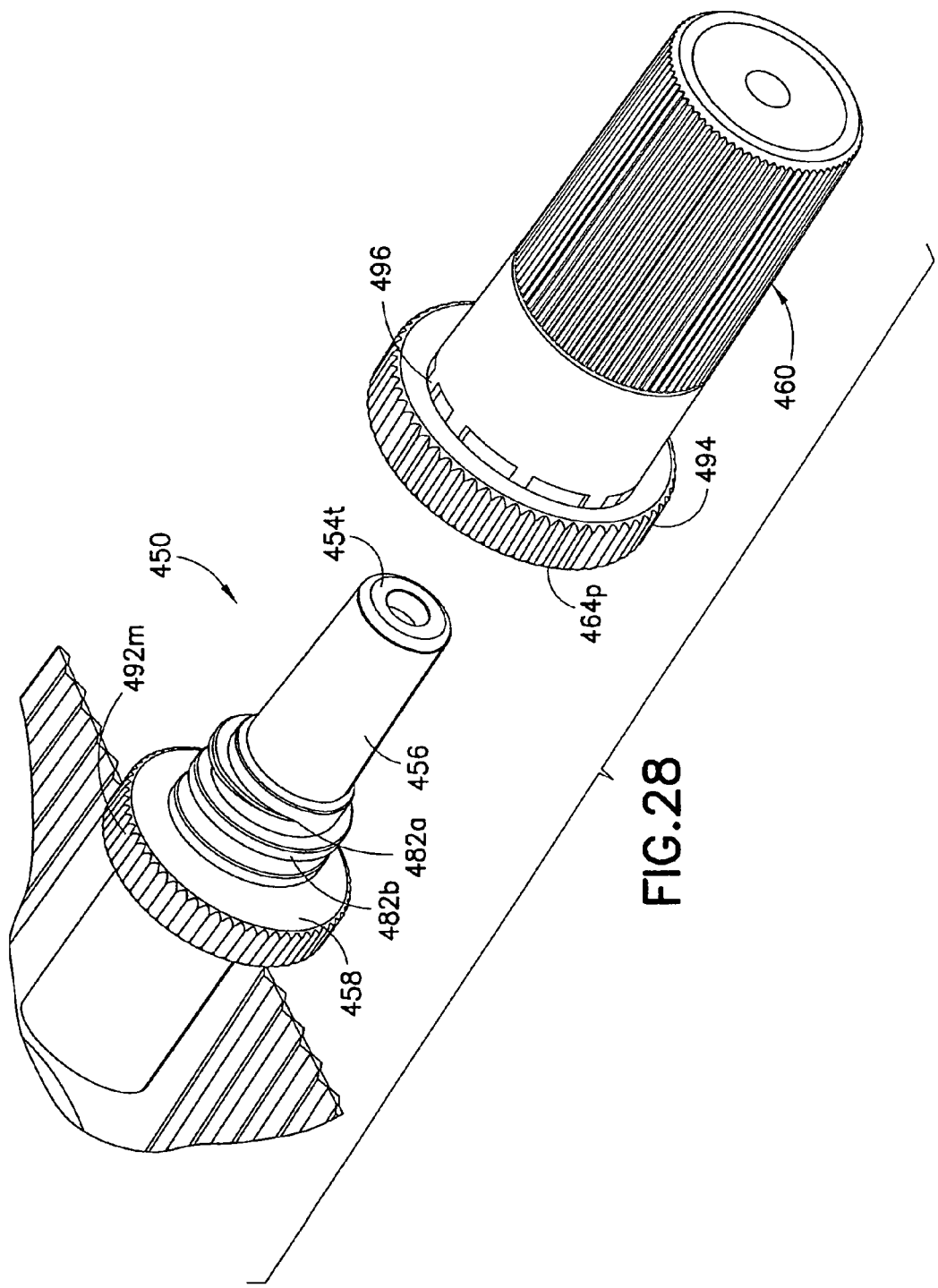
FIG. 28 is a partial exploded front perspective view of the injection device shown in FIG. 26 before being assembled.

As FIG. 23 shows, the injection device 310 can be provided with a fastener 390 to assist in retaining the shield cap 360 in the first position and prevent such shield cap 360 from disengaging with the male luer fitting 350 caused by either operational error or environmental disturbance. In one example, the male luer fitting 350 is provided with a locking structure 392m, such as serrated edges, as best shown in FIG. 24. The shield cap 360 is formed with a matching locking structure 392s, e.g., serrated edges, which, once matched with the locking structure 392m on the male luer fitting 350, prevent unintentional rotation of the shield cap 360 relative to the male luer fitting 350. As a result, the risk of unintended disengagement of the male luer fitting 350 and the shield cap 360 can be reduced.

If desired, one or more additional seals can be provided in this embodiment to enhance the sealing of the contact portion 356 of the male luer fitting 350. In one example as is shown in FIG. 23, the male luer fitting 350 is formed with a circumferential shoulder 386m to contact or otherwise engage with a corresponding internal circumferential shoulder 386s formed inside the shield cap 360. Such additional seals 386m, 386s can further block alien matter passing through the matching locking structures or serrated edges 392m, 392s and/or the matching threads 382, 384 between the male luer fitting 350 and the shield cap 360.

To assemble the injection device 310, the shield cap 360 is screwed or threaded onto the male luer fitting 350, such as in a clockwise direction, so that the matching threads 382, 384 are engaged with and sealed against each other to protect the contacting portion 356 against outside contamination. In the meantime, the first seal 370 on the closed end 364c inside the shield cap 360 is plugged or seated into the channel 352 at the luer tip 354t of the male luer fitting 350 and thereby seals the medicament inside the reservoir 346. The shield cap 360 is further urged onto the male luer fitting 350 until the fastener 390 is engaged. For example, the matching locking structures 392m, 392s can be engaged with each other to retain the first and second seals 370, 380 in the first position without being disturbed by unintentional forces acting on the injection device 310.

A description of exemplary usage of the injection device 310 of the present invention is provided below. It should be understood by a person of ordinary skill in the art that the following description is provided as an illustrative and non-limiting example.

To activate the injection device 310, an operator twists the shield cap 360 in the counterclockwise direction to disengage the fastener 390. For example, the operator can twist the shield cap 360 to cause the serrated threads 392m, 392s to override and disengage from each other. The operator continues to twist or rotate the shield cap 360 in the counterclockwise direction until the matching threads 382, 384 disengage from each other. At the same time, the first seal 370 is axially pulled out from the channel 352 in the male luer fitting 350 to activate the reservoir 346. When the first and second seals 370, 380 are released, the shield cap 360, together with the attached first seal 370 is removed from the contact portion 356 of the male luer fitting 350 to expose the contact portion 356 and the luer tip 354t. The contaminant free male luer fitting 350 of the injection device 310 is then fitted directly in a female luer connector (not shown). To deliver the medicament, the operator squeezes the reservoir 346.

The first and second connecting structure 382, 384 and seals 370, 380 and the fastener 390 can alternatively be formed in accordance with the connecting structures and seals described in the other embodiments of the present application.

FIGS. 26 to 30 illustrate an injection device 410 formed as a variation of injection device 310 described above. In the injection device 410, the syringe body 437, the male luer fitting 450, and the shield cap 460 are similarly formed to their respective counterparts 137, 150, and 160 described in the first embodiment. In addition, the first seal 470 in the injection device 410 is formed similarly to the first seal 370 described in the above embodiment. The differences between the injection device 410 and the previous embodiments are described in details below.

The second seal 480 in the injection device 410 can comprise matching threads 482, 484 formed on the respective male luer fitting 450 and shield cap 460. The second seal 480 is formed between said male luer fitting 450 and said shield cap 460 in the first position to prevent alien matter to pass through and contaminate the contacting portion 456 of the luer tip 454t of said male luer fitting 450. In the example shown in FIG. 27, the first connecting structure 482 can be in the form of at least one circumferential rib or spiral thread 482a, 482b arranged on said male luer fitting 450 between said base end 454b and said luer tip 454t. The second connecting structure 484 can be in the form of an internal circumferential rib or spiral thread 484a formed inside the shield cap 460 at its open end 464p. The first and second connecting structures 482a, 482b, 484 can interlock with each other to seal the interior of the shield cap 460 and thus seal the contact portion 456 of the male luer fitting 450 from contamination.

In addition, a fastener 490 can be provided in the injection device 410 to retain the first and second seals 470, 480 in the first position. In one example, the fastener 490 is in the form of a tamper seal, which can include a first collar member 494 connected to the open end 464p of the shield cap 460 through a number of tamper-proof tabs 496. The collar member 494 is formed to fit onto the circumferential surface of the flange 458 on the male luer fitting 450. The interface of the collar member 494 and the flange 458 can be adapted to cooperate with each other allowing only a one-way relative rotation therebetween. For example, the interface of the collar member 494 and the flange 458 can be a one-way locking thread 492m, 492s to allow the shield cap 460 to be twisted onto the male luer fitting 450 and prevent the shield cap 460 from rotating in an opposite direction, thereby loosened from the male luer fitting 450.

If desired, one or more of the circumferential surfaces of the shield cap 460 or collar 494 can be provided with additional traction and grip, such as a knurled grip, to the operator when handling the injection device 410. Additional traction member, such as longitudinal ribs or grooves can be additionally or alternatively provided for the same purpose.

To assemble the injection device 410, the shield cap 460 is screwed onto the male luer fitting 450, such as in a clockwise direction, so that the matching threads 482, 484 are engaged with and sealed against each other to protect the contacting portion 456 against outside contamination. In the meantime, the first seal 470 on the closed end 464c inside the shield cap 460 is plugged or seated into the channel 452 at the luer tip 454t of the male luer fitting 450 to thereby seal the medicament inside the reservoir 446. The shield cap 460 is then further screwed onto the male luer fitting 450 until the fastener 490 is engaged. For example, the matching locking threads 492m, 492s are engaged with each other to prevent the first and second seals 470, 480 from departing from the first position. The tamper-proof tabs 496 will break to indicate unintended activation of the injection device 410.

A description of exemplary usage of the injection device 410 of the present invention is provided below. It should be understood by a person of ordinary skill in the art that the following description is provided as an illustrative and non-limiting example.

Figure 29:
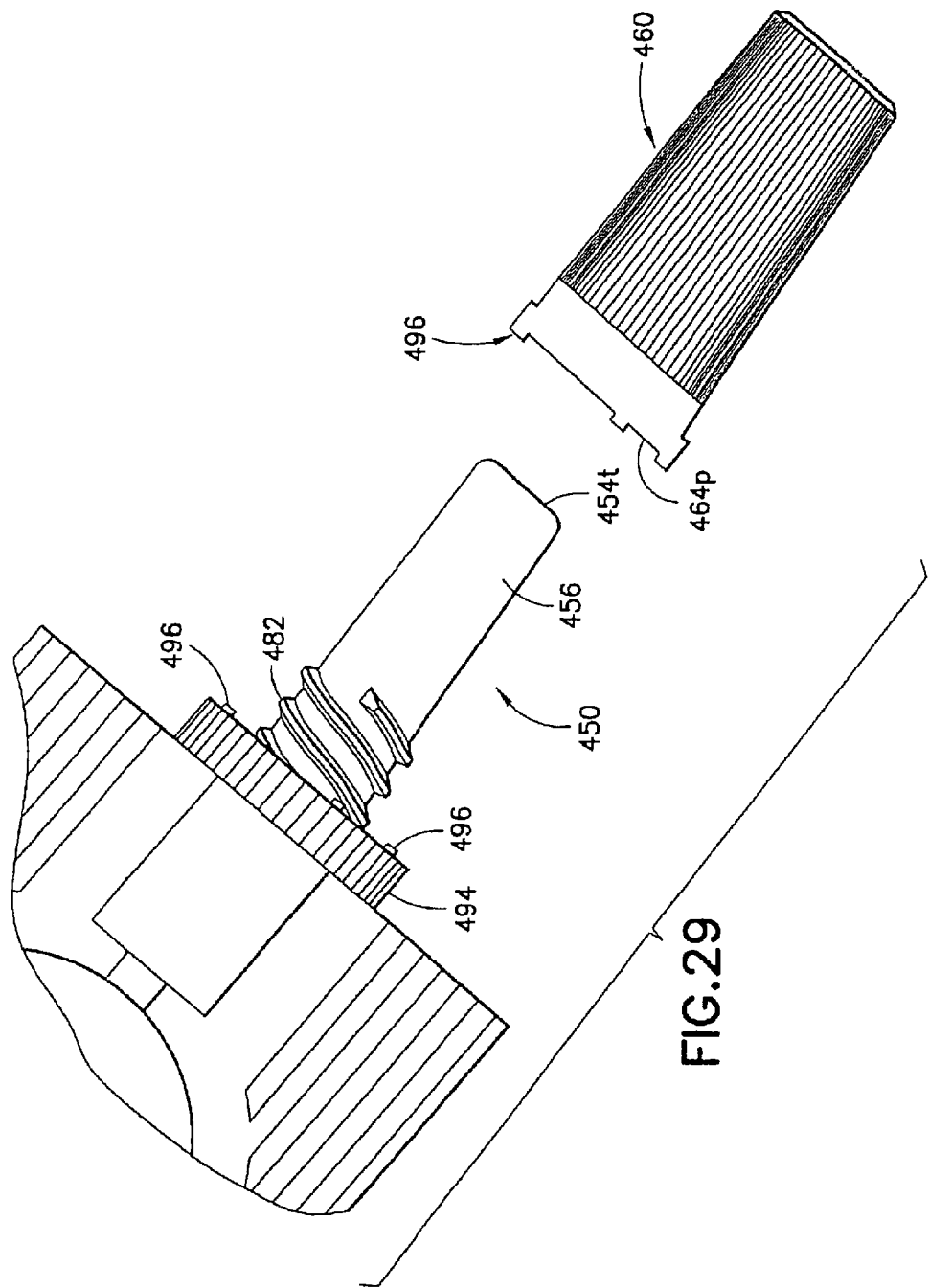
FIG. 29 is a partial perspective view of the injection device shown in FIG. 26 after the shield cap breaks off from the male luer fitting.
Figure 30:
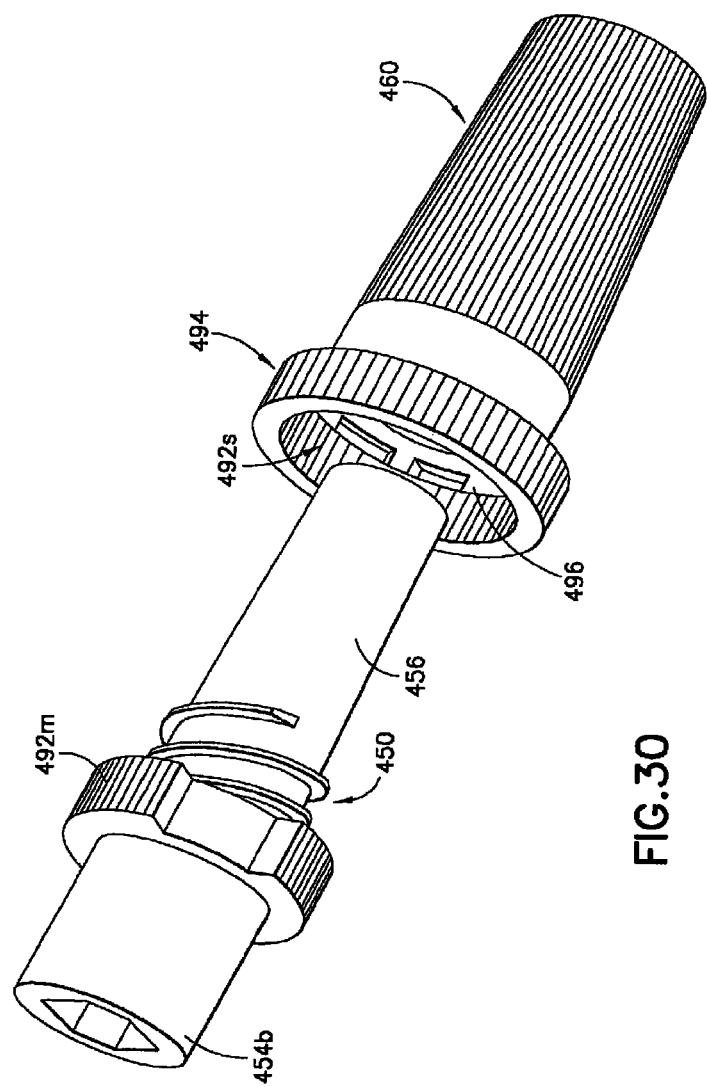
FIG. 30 is a partial exploded rear perspective view of the injection device shown in FIG. 26 before being assembled.

To activate the injection device 410, an operator first inspects the tamper-proof tabs 496 to ensure that they have not been broken. The shield cap 460 is then twisted in the counterclockwise direction to disengage the fastener 490. For example, the operator can twist the shield cap 460 to break the tamper-proof tabs 496, as is shown in FIG. 29. The shield cap 460 can then be removed from the contact portion 456 of the male luer fitting 450, while pulling or unseating the first seal 470 from the channel 452 of the male luer fitting 450. The male luer fitting 450 is then fitted directly in a female luer connector (not shown). The medicament is then delivered by the operator squeezing or compressing the reservoir 446.

The first and second connecting structure 482, 484 and seals 470, 480 and the fastener 490 can alternatively be formed by the connecting structures and seals disclosed by the above embodiments.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. An injection device with a luer fitting, the injection device comprising:
 a compressible syringe body comprising two flexible sheets defining a reservoir;
 a male luer fitting that is substantially cylindrical having a tapered outer surface, a base end and a luer tip at an end of said male luer fitting opposing said base end, said male luer fitting provided as a separate component from the syringe body, said base end connected to and sealed within said flexible sheets, said male luer fitting having a channel therethrough for conducting contents of the reservoir;
 a first connecting structure arranged on said tapered outer surface of the male luer fitting between said base end and said luer tip;

a shield cap having a generally cylindrical shaped portion arranged on the male luer fitting at a first position relative to said male luer fitting prior to use of the injection device, said shield cap having a second connecting structure on an inner surface of its generally cylindrical shaped portion and interacting with said first connecting structure to prevent inadvertent movement of said shield cap relative to said male luer fitting when said shield cap is arranged at said first position;

a first seal comprising a pierceable membrane sealing said channel at said luer tip and preventing leakage therethrough of content from said reservoir at least when the shield cap is at said first position; and a second seal between said shield cap and said male luer fitting sealing the tapered outer surface and the luer tip of said male luer fitting from outside contamination, said second seal formed by said first and second connecting structures when the shield cap is arranged at the first position, wherein said shield cap is movable relative to said male luer fitting to a second position from said first position, said first seal being pierced by movement of said shield cap from said first position to said second position, wherein said first and second connecting structures each comprise at least one circumferential rib or raised ring.

2. The injection device of claim 1, wherein said shield cap is removable from said male luer fitting from said second position, said male luer fitting being capable of delivering the contents of the reservoir after said shield cap is removed from said male luer fitting from said second position.

3. The injection device of claim 1, wherein said shield cap comprises a sharp tip facing said luer tip when said shield cap is in said first position.

4. The injection device of claim 3, wherein said sharp tip punctures or cuts said first seal when said shield cap is moved from said first position to said second position.

5. The injection device of claim 3, wherein said sharp tip comprises a needle bonded to said shield cap.

6. A method of dispensing contents of a compressible reservoir of an injection device through a male luer fitting that is substantially cylindrical having a tapered outer surface connected to the injection device, said method comprising:

sealing a base end of said substantially cylindrical male luer fitting within two flexible sheets of a syringe body of the injection device;

placing a shield cap at a first position on said male luer fitting;

sealing, with a first seal, a luer tip preventing leakage therethrough of content from the reservoir of the syringe body at least when the shield cap is at the first position;

sealing, with a second seal, the tapered outer surface of the luer tip from outside contamination by a second seal formed by first and second connecting structures on the tapered outer surface of the male luer fitting and an inner surface of the shield cap, respectively, when the shield cap is arranged at the first position;

moving the shield cap on the male luer fitting from a first position to a second position to open at least the first seal; and removing the shield cap from the second position, whereby the contents of the reservoir are capable of being dispensed after the shield cap is removed from the second position, wherein the second seal is formed by at least one rib or circumferential ring arranged on each of the shield cap and the male luer fitting.

7. The method of claim 6, wherein the shield cap includes a sharp tip facing the first seal when the shield cap is in the first position.

8. The method of claim 7, wherein the sharp tip cuts through or pierces the first seal during movement of the shield cap from the first position to the second position.

9. The method of claim 6, wherein the step of moving comprises moving the shield cap longitudinally relative to the male luer fitting.

* * * * *